US011944297B2

(12) United States Patent
Shelton, IV et al.

(10) Patent No.: US 11,944,297 B2
(45) Date of Patent: Apr. 2, 2024

(54) VARIABLE RESPONSE MOTOR CONTROL ALGORITHM FOR POWERED SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US)

(73) Assignee: Cilag GmbH International, Zug (CH)

( * ) Notice: Subject to any disclaimer, the term of this patent is extended or adjusted under 35 U.S.C. 154(b) by 18 days.

(21) Appl. No.: 17/402,677

(22) Filed: Aug. 16, 2021

(65) Prior Publication Data
US 2023/0048444 A1  Feb. 16, 2023

(51) Int. Cl.
*A61B 17/072* (2006.01)
*A61B 34/30* (2016.01)

(52) U.S. Cl.
CPC ............ *A61B 17/072* (2013.01); *A61B 34/30* (2016.02); *A61B 2017/07271* (2013.01); *A61B 2017/07285* (2013.01)

(58) Field of Classification Search
CPC .......................................... A61B 2017/07285
USPC ....................................................... 227/180.1
See application file for complete search history.

(56) References Cited

U.S. PATENT DOCUMENTS

| 5,129,570 | A  | 7/1992  | Schulze et al.    |
| 7,404,508 | B2 | 7/2008  | Smith et al.      |
| 7,434,715 | B2 | 10/2008 | Shelton, IV et al.|
| 7,721,930 | B2 | 5/2010  | McKenna et al.    |
| 7,810,692 | B2 | 10/2010 | Hall et al.       |
| 7,832,408 | B2 | 11/2010 | Shelton, IV et al.|
| 7,845,537 | B2 | 12/2010 | Shelton, IV et al.|
| 8,083,120 | B2 | 12/2011 | Shelton, IV et al.|

(Continued)

FOREIGN PATENT DOCUMENTS

| EP | 3225190 A2 | 10/2017 |
| EP | 3231374 A1 | 10/2017 |

(Continued)

OTHER PUBLICATIONS

U.S. Appl. No. 17/402,674.

(Continued)

*Primary Examiner* — Thanh K Truong
*Assistant Examiner* — Patrick B Fry
(74) *Attorney, Agent, or Firm* — Frost Brown Todd LLP

(57) ABSTRACT

An apparatus includes an end effector, a motor, and a processing unit. The processing unit is configured to activate the motor to distally advance a firing member within a body of the end effector. The processing unit is further configured to detect an initiation condition. In response to detecting the initiation condition, the processing unit is configured to activate an algorithmic bumping mode. The bumping mode includes activating the motor to advance the firing member distally with a first plurality starting and stopping motions at a first rate and a first power level. The bumping mode further includes activating the motor to retract the firing member proximally with a second plurality of starting and stopping motions at a second rate and a second power level. The first rate is different than the second rate. The first power level is different than the second power level.

19 Claims, 22 Drawing Sheets

(56) References Cited

U.S. PATENT DOCUMENTS

| | | |
|---|---|---|
| 8,210,411 B2 | 7/2012 | Yates et al. |
| 8,408,439 B2 | 4/2013 | Huang et al. |
| 8,453,914 B2 | 6/2013 | Laurent et al. |
| 8,708,213 B2 | 4/2014 | Shelton, IV et al. |
| 9,060,770 B2 | 6/2015 | Shelton, IV et al. |
| 9,186,142 B2 | 11/2015 | Fanelli et al. |
| 9,517,065 B2 | 12/2016 | Simms et al. |
| 9,615,888 B2 * | 4/2017 | Manzo .................. A61B 34/74 |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,487 B2 | 12/2017 | Dachs, II |
| 10,011,018 B2 | 7/2018 | McGrogan et al. |
| 10,092,292 B2 | 10/2018 | Boudreaux et al. |
| 10,271,847 B2 * | 4/2019 | Racenet .......... A61B 17/07207 |
| 10,307,170 B2 | 6/2019 | Parfett et al. |
| 10,441,279 B2 * | 10/2019 | Shelton, IV ......... A61B 17/295 |
| 10,485,621 B2 | 11/2019 | Morrissette et al. |
| 10,537,400 B2 | 1/2020 | Dachs, II et al. |
| 10,610,313 B2 | 4/2020 | Bailey et al. |
| 10,667,809 B2 | 6/2020 | Bakos et al. |
| 10,806,530 B2 | 10/2020 | Liao et al. |
| 10,863,988 B2 | 12/2020 | Patel et al. |
| 11,002,634 B2 * | 5/2021 | Fayfield .............. G01M 13/045 |
| 11,020,138 B2 | 6/2021 | Ragosta |
| 11,026,755 B2 | 6/2021 | Weir et al. |
| 11,076,926 B2 | 8/2021 | Ragosta et al. |
| 11,147,552 B2 | 10/2021 | Burbank et al. |
| 11,166,773 B2 | 11/2021 | Ragosta et al. |
| 11,234,700 B2 | 2/2022 | Ragosta et al. |
| 11,259,884 B2 | 3/2022 | Burbank |
| 2006/0185682 A1 | 8/2006 | Marczyk |
| 2012/0205421 A1 | 8/2012 | Shelton, IV |
| 2012/0209314 A1 | 8/2012 | Weir et al. |
| 2015/0297228 A1 | 10/2015 | Huitema et al. |
| 2016/0361126 A1 | 12/2016 | Schena et al. |
| 2017/0020617 A1 | 1/2017 | Weir et al. |
| 2017/0265865 A1 | 9/2017 | Burbank |
| 2017/0265954 A1 | 9/2017 | Burbank et al. |
| 2017/0333037 A1 | 11/2017 | Wellman et al. |
| 2018/0168756 A1 | 6/2018 | Liao et al. |
| 2018/0271608 A1 | 9/2018 | Ragosta et al. |
| 2018/0310935 A1 | 11/2018 | Wixey |
| 2018/0325606 A1 | 11/2018 | Weir et al. |
| 2018/0344419 A1 | 12/2018 | Dachs, II et al. |
| 2019/0038371 A1 | 2/2019 | Wixey et al. |
| 2019/0076142 A1 | 3/2019 | Wixey |
| 2019/0076143 A1 | 3/2019 | Smith |
| 2019/0167266 A1 | 6/2019 | Patel et al. |
| 2019/0200989 A1 | 7/2019 | Burbank et al. |
| 2019/0206565 A1 | 7/2019 | Shelton, IV |
| 2019/0239967 A1 | 8/2019 | Ragosta et al. |
| 2019/0262088 A1 | 8/2019 | Burbank |
| 2019/0290265 A1 * | 9/2019 | Shelton, IV .............. H02J 7/00 |
| 2020/0138529 A1 | 5/2020 | Ragosta et al. |
| 2020/0397430 A1 | 12/2020 | Patel et al. |
| 2020/0405301 A1 | 12/2020 | Shelton, IV et al. |
| 2021/0393340 A1 | 12/2021 | Beckman et al. |
| 2021/0401433 A1 | 12/2021 | Freidel et al. |

FOREIGN PATENT DOCUMENTS

| | | |
|---|---|---|
| EP | 3545881 A1 | 10/2019 |
| WO | WO 2015/153642 A1 | 10/2015 |
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,675.
U.S. Appl. No. 17/402,679.
U.S. Appl. No. 17/402,695.
U.S. Appl. No. 17/402,701.
U.S. Appl. No. 17/402,703.
U.S. Appl. No. 17/402,720.
U.S. Appl. No. 17/402,732.
U.S. Appl. No. 17/402,738.
U.S. Appl. No. 17/402,744.
U.S. Appl. No. 17/402,749.
U.S. Appl. No. 17/402,759.
U.S. Appl. No. 17/088,941, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
International Search Report and Written Opinion dated Dec. 13, 2022 for Application No. PCT/IB2022/057614, 17 pgs.

* cited by examiner

| Device | Max Motor | Cycle Operation Counts | | | | | Event Count | |
|---|---|---|---|---|---|---|---|---|
| Cycle/Usage | Power Limit | Motor Current Limit Exceeded | Motor Temperature Limit Exceeded | Impact/Bumping Forward Cycles | Impact/Bumping Reverse Cycles | Wait Period | Recoverable | Sum of Non-Recoverable |
| 1 | 100% | 1 | -- | 1 | 1 | 1 | -- | 4 |
| 2 | 93% | 1 | -- | -- | -- | -- | 1 | 4 |
| 3 | 91% | 1 | -- | 1 | 1 | 1 | -- | 6 |
| 4 | 86% | 2 | 1 | -- | -- | -- | -- | 11 |
| 5 | 80% | -- | -- | -- | -- | -- | -- | 11 |
| 6 | 79% | 2 | -- | -- | -- | -- | 2 | 11 |
| 7 | 77% | 3 | 2 | 2 | 2 | 2 | 1 | 21 |
| 8 | 65% | -- | -- | -- | -- | -- | -- | 21 |
| 9 | 64% | 1 | -- | 1 | -- | -- | -- | 27 |
| 10 | 55% | X | X | X | X | X | X | X |
| 11 | X | X | X | X | X | X | X | X |
| 12 | X | X | X | X | X | X | X | X |
| 13 | X | X | X | X | X | X | X | X |
| 14 | X | X | X | X | X | X | X | X |
| 15 | X | X | X | X | X | X | X | X |

VARIABLE RESPONSE MOTOR CONTROL ALGORITHM FOR POWERED SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 25 depicts an exemplary data table that may be utilized in conjunction with the end-of-life algorithm of FIG. 24.

Figure 1:
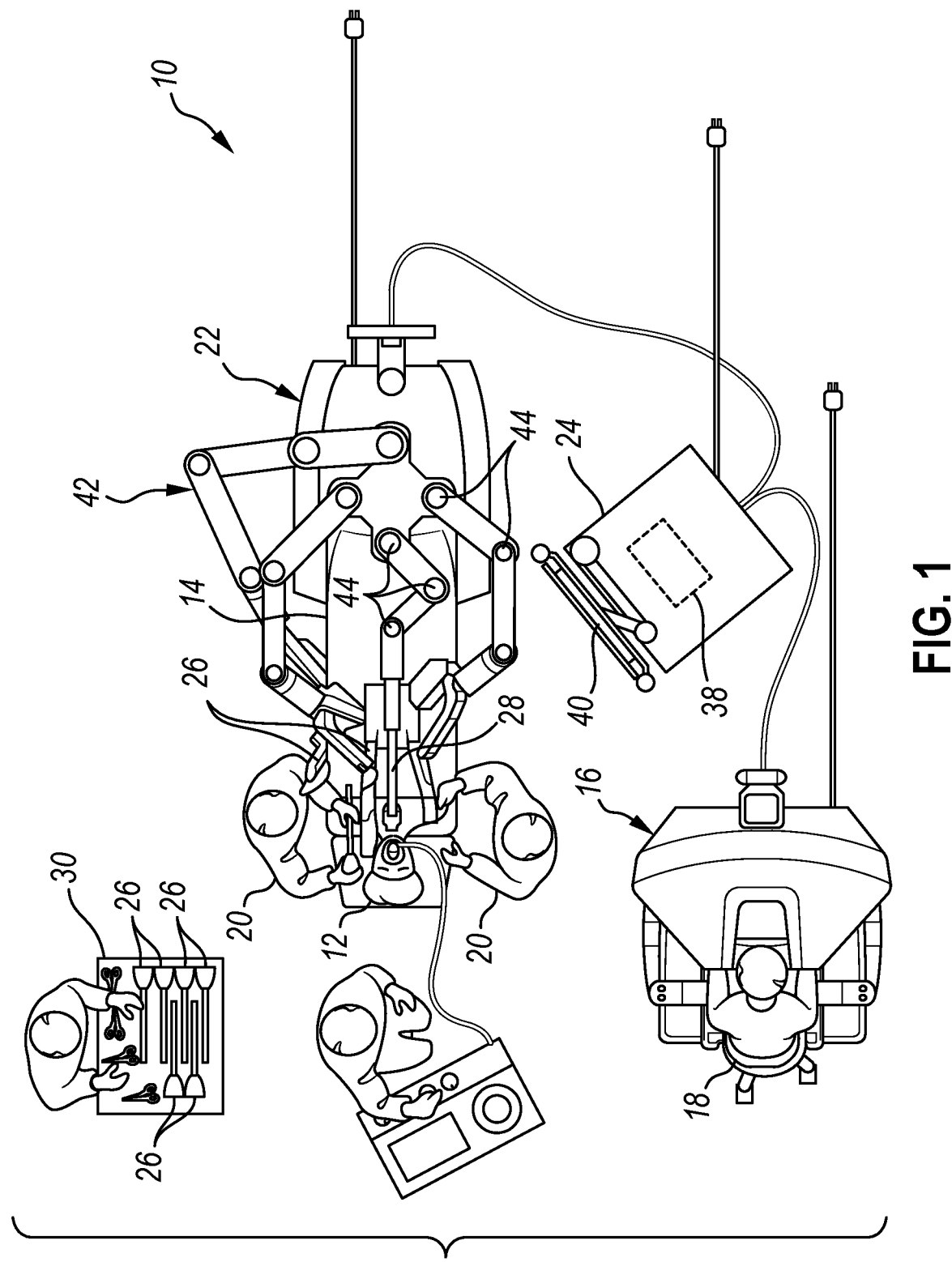
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No.

10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019; U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
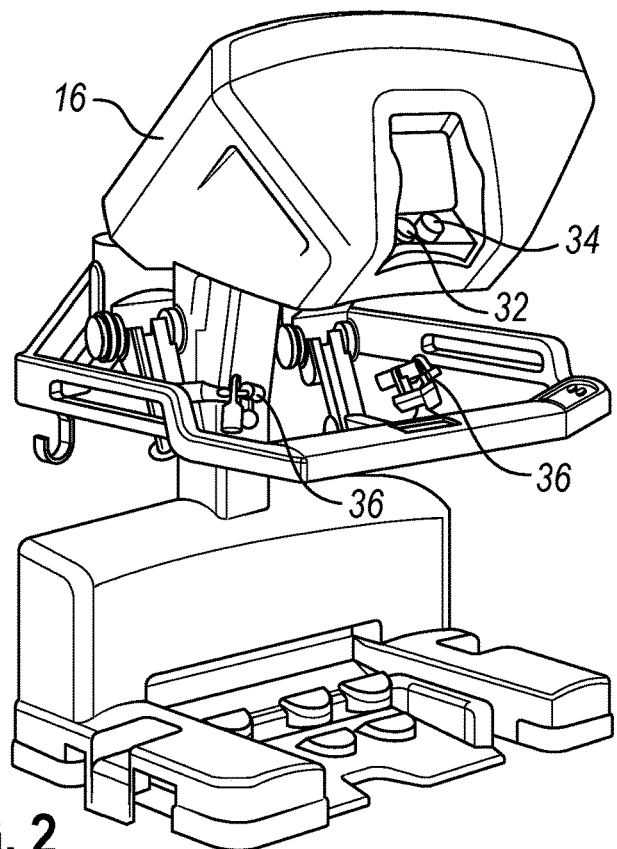
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
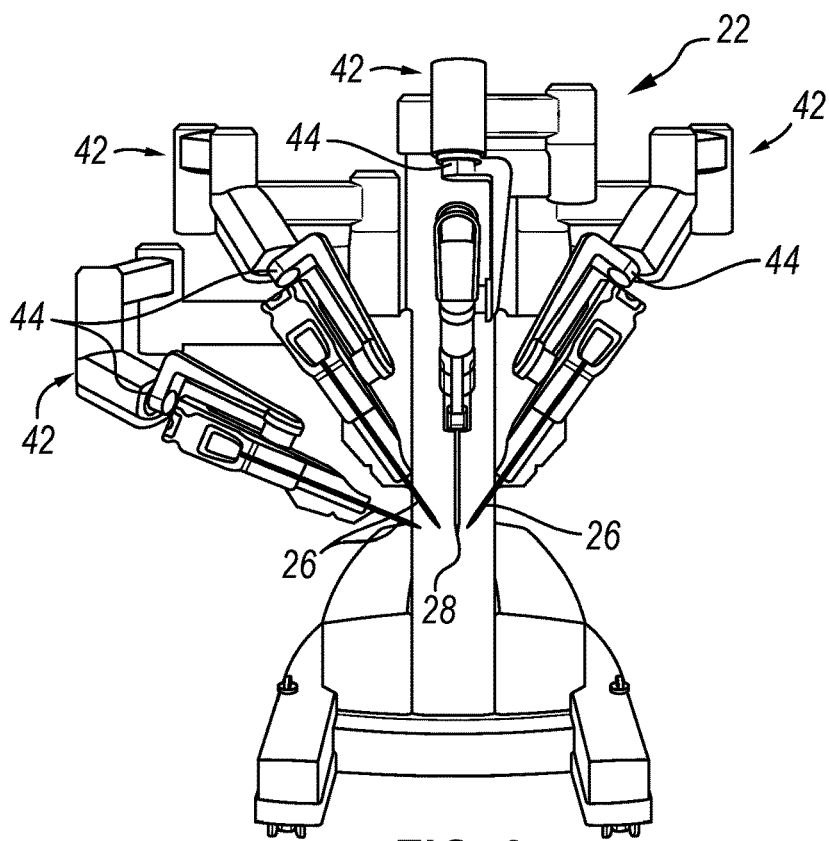
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
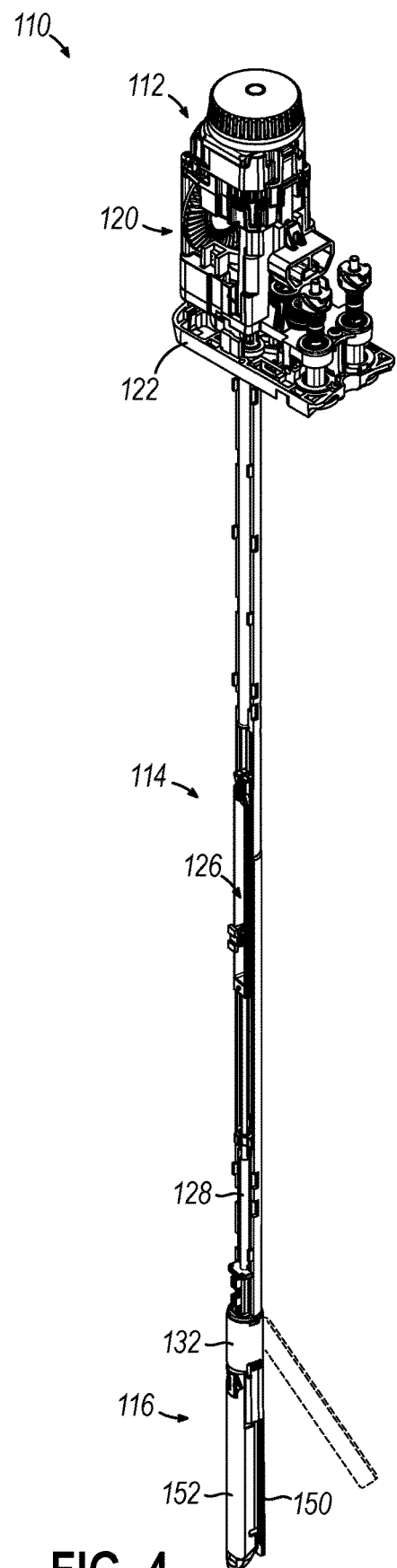
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
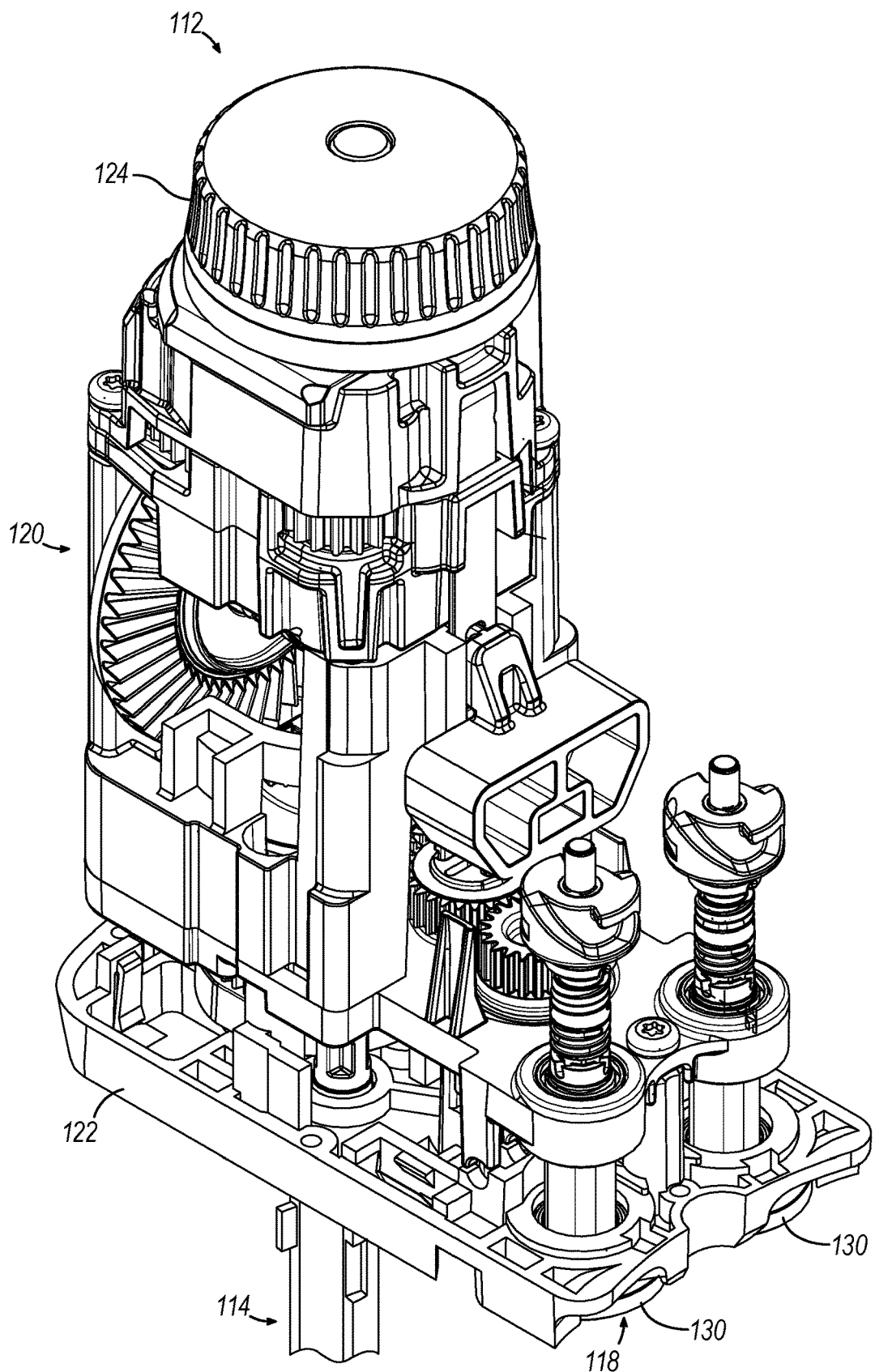
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
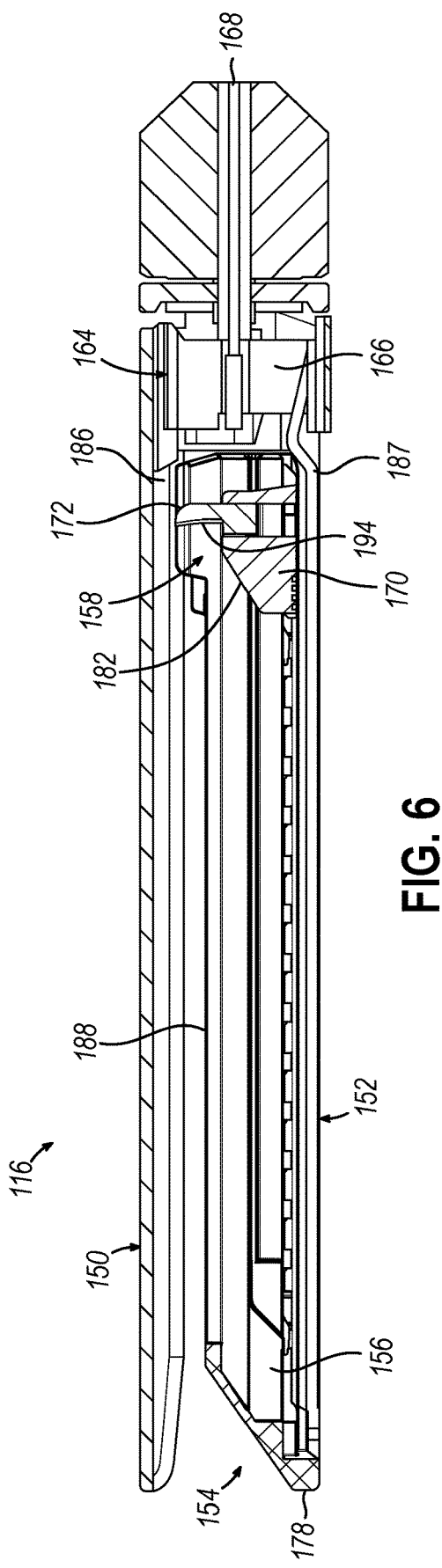
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
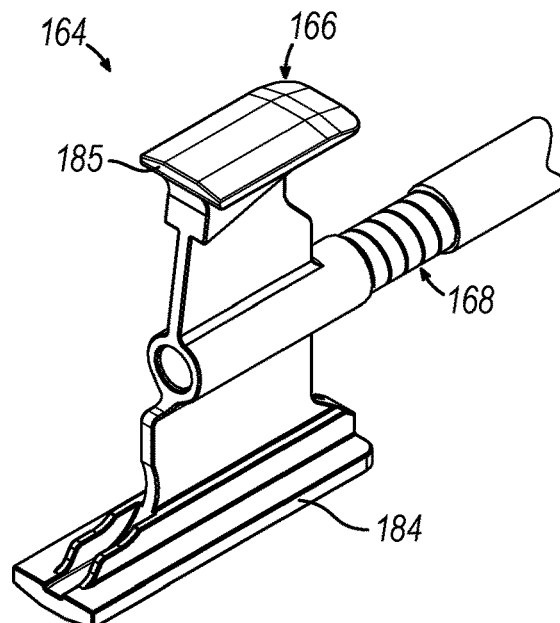
FIG. 8 depicts a driving assembly configured for use with the staple cartridge of FIG. 7.
Figure 9:
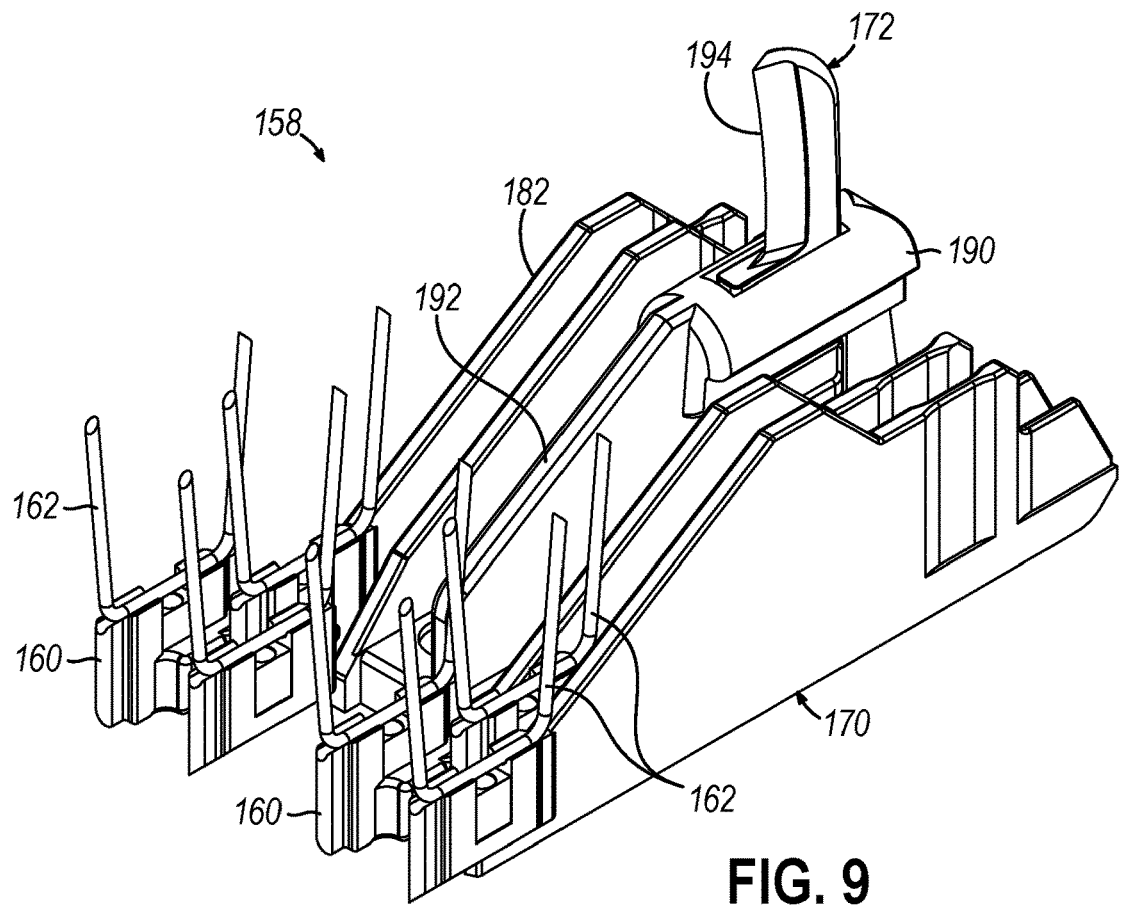
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
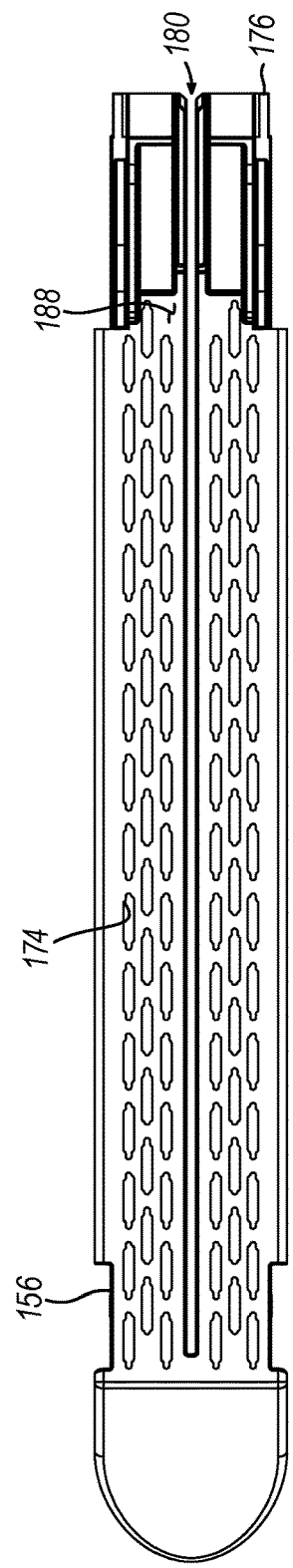
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed; and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
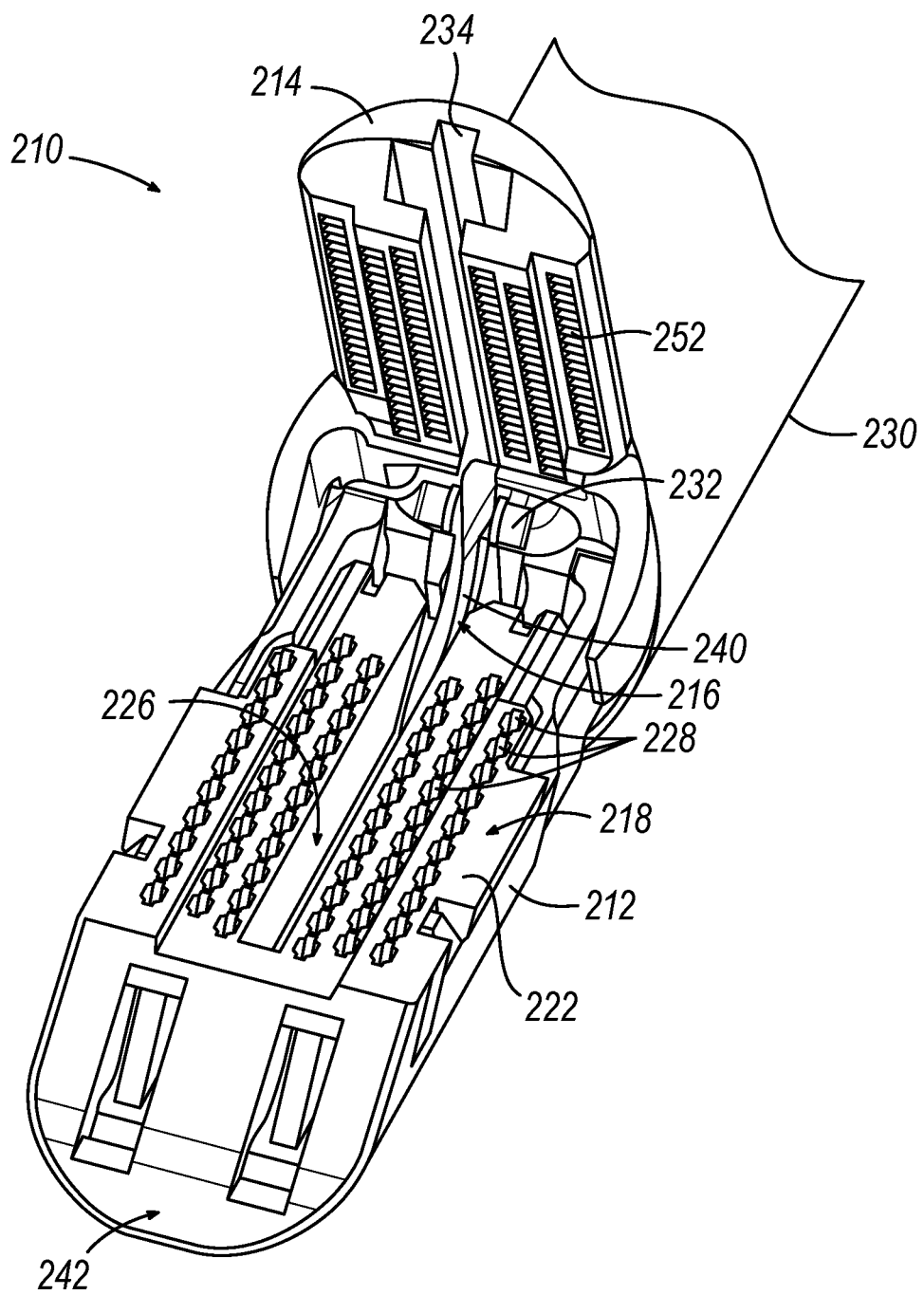
FIG. 10 depicts a second exemplary end effector that may be configured for use with the robotic surgical system of FIG. 1.
Figure 11:
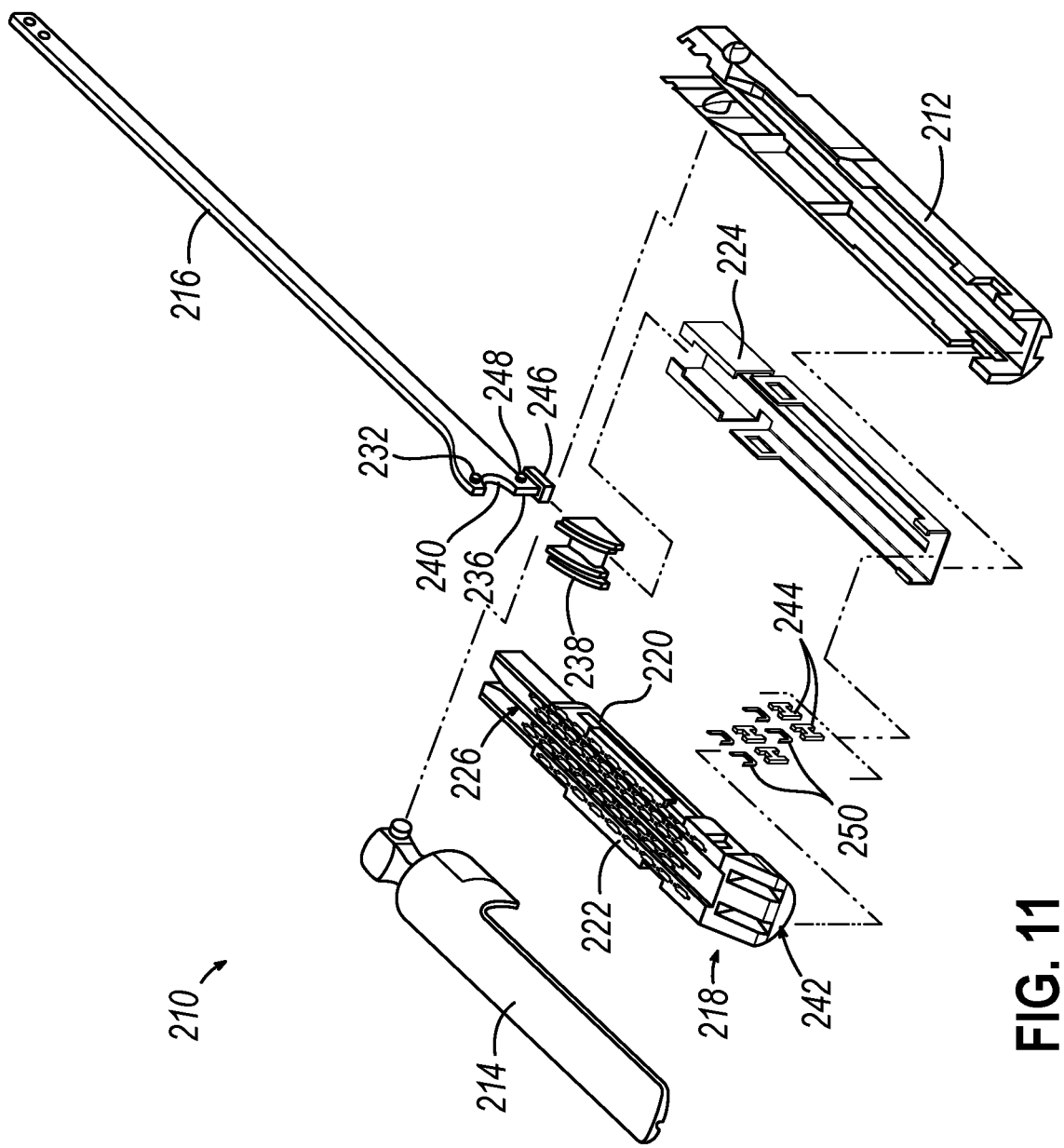
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin (232) of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, the disclosure of which is hereby incorporated by reference herein in its entirety.

It will be appreciated that any one or more of the teachings described below may be combined with any one or more of the teachings described above in connection with FIGS. 1-11.

II. Exemplary Motor Control Algorithms for Powered Surgical Stapler

Figure 12:
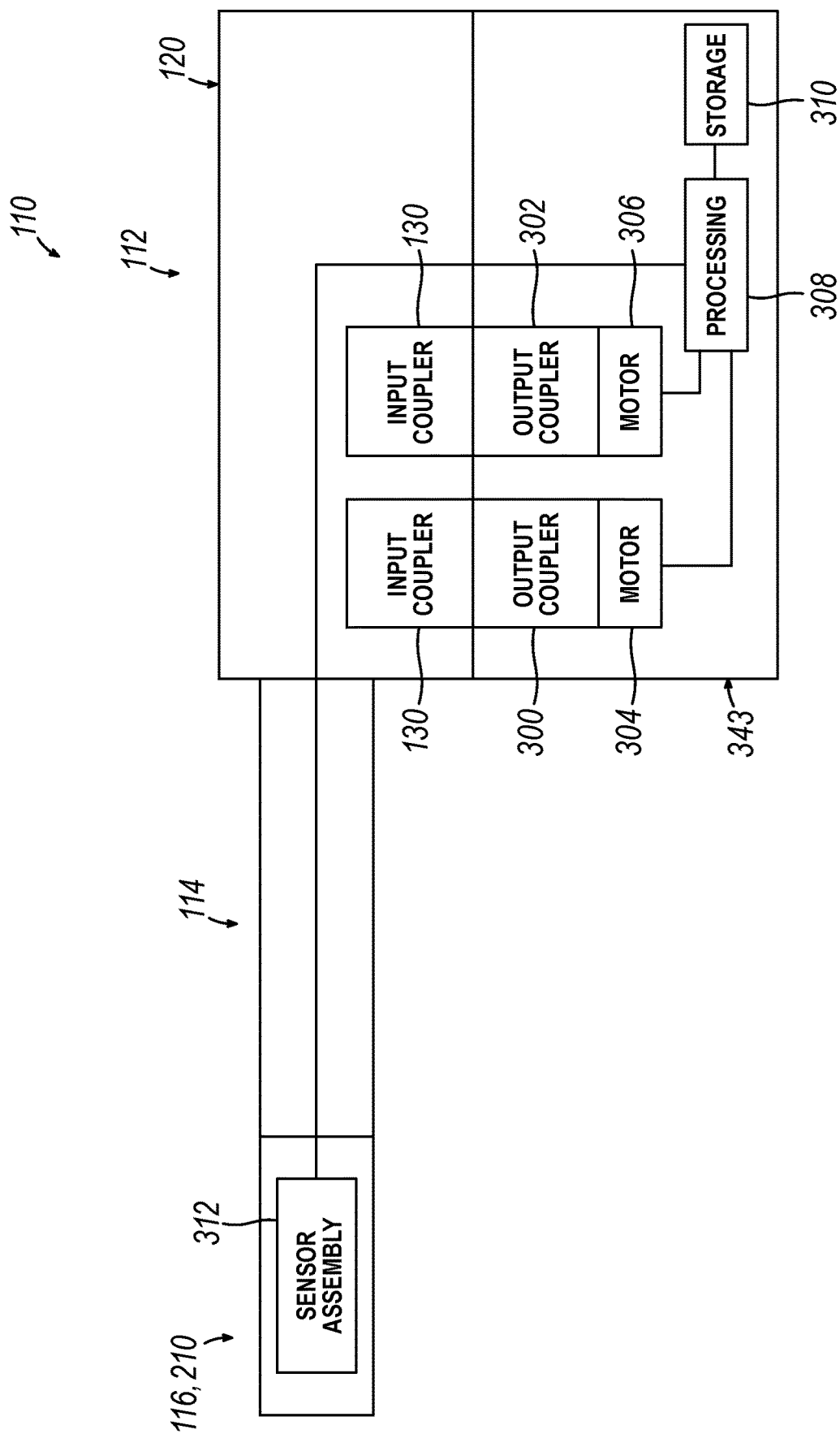
FIG. 12 depicts a schematic view of a robotic arm coupled with the surgical instrument of FIG. 4.

FIG. 12 shows a schematic view of instrument (110) suitably coupled with an exemplary robotic arm (342). Robotic arm (342) may be substantially similar to robotic arm (42) described above, with differences elaborated below. Therefore, it should be understood that robotic arm (342) may suitably interact with robotic surgical system (10) described above such that a medical professional operator may utilize robotic surgical system (10) to control instrument (110) via robotic arm (342), input control devices (36) of surgeon's console (16), and any other suitable intermediate components as would be apparent to one skilled in the art in view of the teachings herein.

As mentioned above, instrument base (112) includes input couplers (130). Input couplers (130) are configured to interface with and be driven by corresponding output couplers (300, 302) of robotic arm (342). Output couplers (300, 302) maybe actuated via one or more robotic motors (304, 306), respectively, which may be controlled by a processing unit (308) in communication with input control devices (36) of surgeon's console (16). Processing unit (308) may receive instructions from input control devices (36) in order to actuate robotic motors (304, 306) and corresponding output couplers (300, 302). While operatively interfacing with input couplers (130), output couplers (300, 302) of robotic arm (342) may be used to actuate selective portions of either end effector (116, 210) in accordance with the description herein. Therefore, robotic motor(s) (304, 306) in communication with output couplers (300, 302) of robotic arm (342) may be used to suitably control end effector (116, 210) in clamping, severing, and stapling tissue in accordance with the description herein.

Output couplers (300, 302) and input couplers (130) may include any suitable components as would be apparent to one skilled in the art in view of the teachings herein. While in the current example, two input couplers (130) and two respective output couplers (300, 302) are used, any suitable number of input couplers (130) and any suitable number of output couplers (300, 302) may be utilized as would be apparent to one skilled in the art in view of the teachings herein.

Robotic motors (304, 306) may include any suitable components as would be apparent to one skilled in the art in view of the teachings herein. Robotic motors (304, 306) and/or processing unit (308) may include suitable components to measure suitable output characteristics, operating data, etc., of robotic motors (304, 306). For example, robotic motors (304, 306) may include components configured to measure motor temperature, motor displacement, the electrical current used by robotic motors (304, 306), motor power usage (either in a specified unit or represented as a percentage compared to a maximum motor power usage), etc., and may communicate such operating data to processing unit (308) for use of such data in accordance with the description herein.

Processing unit (308) may also be in communication with a storage device (310) such that processing unit (308) may communicate data to storage device (310), and such that processing unit (308) may access and utilize data stored on storage device (310). Processing unit (308) and storage device (310) may contain any suitable number of components as would be apparent to one skilled in the art in view of the teachings herein.

Processing unit (308) may utilize data contained in storage device (310) in order to establish operational parameters for robotic arm (342) while controlling a specific instrument (110). Storage device (310) may be configured to store information related to a specific instrument (110), such as any suitable data accumulated during exemplary use of a specific instrument (110) as would be apparent to one skilled in the art in view of the teachings herein. In some instances, a specific instrument (110) may have an identifiable chip or other electronic device that notifies processing unit (308) of the specific instrument (110) that is coupled with robotic arm (342), therefore allowing processing unit (308) to track the specific instrument (110) and data stored on storage device (310) related to the specific instrument (110). In some instances, the specific instrument (110) may include its own storage device (310) that establishes communication with processing unit (308) when instrument (110) is initially coupled with robotic arm (342). In such instances, information regarding prior use of a specific instrument (110) may be stored on that instrument's specific storage device and accessed by processing unit (308) when the specific instrument (110) is coupled to robotic arm (342).

Processing unit (308) may recall and utilize data stored on storage device (310) related to specific instruments (110) when that specific instrument (110) is coupled to robotic arm (342) for exemplary use in accordance with the description herein. For example, storage device (310) may be configured to store the number of times a specific instrument (110) is used and fired in accordance with the teachings herein. As another example, processing unit (308) may be configured to determine when a noteworthy event occurred during operation of a specific instrument (110) and communicate such a noteworthy event to storage device (310) such that processing unit (308) may recall and utilize such noteworthy events when the specific instrument (110) is recoupled and reused with robotic arm (342) in accordance with the teachings herein.

While in the current example, storage device (310) is housed within robotic arm (342), storage device (310) may be associated with any suitable component as would be apparent to one skilled in the art in view of the teachings herein. For example, storage device (310) may be housed within instrument (110) such that storage device (310) may selectively establish communication with processing unit (308) while instrument (110) is coupled to robotic arm (342). As another example, storage device (310) may be associated with surgeon's console (16). In other instances, multiple storage devices (310) may be utilized, each associated with various components, such that each storage device (310) stores data related to the respective specific component.

As mentioned above, instrument (110) may include either end effector (116, 210) operatively attached to the distal end of shaft assembly (114). End effector (116, 210) may include a sensor assembly (312) configured to establish communication with processing unit (308) when instrument (110) is operatively coupled with robotic arm (342). Therefore, data obtained from sensor assembly (312) may be stored on storage device (310) for later access by processing unit (308). Sensor assembly (312) may include one or more sensors configured to measure any suitable data as would be apparent to one skilled in the art in view of the teachings herein. For instance, sensor assembly (312) may be configured to measure a tissue load imparted on the jaws (150, 152, 212, 214) while grasping tissue in accordance with the description herein. Additionally, or alternatively, sensor assembly (312) may be configured to measure the locations tissue is in contact with jaws (150, 152, 212, 214) while grasping tissue in accordance with the description herein.

In some instances, each input coupler (130) is controlled by a different motor (304, 306) may be used to perform separate functions. For example, in instances where end effector (210) is operatively attached to the distal end of shaft assembly (114), first motor (304) and the respective output coupler (300) and input coupler (130) may be utilized to actuate firing beam (216); while second motor (306) and the respective output coupler (302) and input coupler (130) may be utilized to acuate colure tube (not shown) and closure ring (230).

A. Exemplary Motor Control Algorithm Utilizing Impulse Actuation

During the firing process of either end effector (116, 210) in accordance with the description herein, driving assembly (164) (see FIG. 8) or firing beam (216) (see FIG. 11) may become undesirably stuck in a longitudinal position relative to staple cartridge (154, 218) such that driving assembly (164) or firing beam (216) relative to staple cartridge (154, 218) is inhibited beyond a tolerable degree. For example, during distal advancement of pusher member (166) (see FIG. 8) in accordance with the description herein, flanges (184, 185) may overly engage or dig into portions of staple cartridge (154) and/or jaws (150, 152) defining associated longitudinal slots (186, 187), thereby inhibiting suitable movement due to an undesirable amount of frictional braking force. As another example, during distal advancement of firing beam (216), upper pin (232) or firing beam cap (246) (see FIG. 11) may overly engage or dig into portions of staple cartridge (218) defining longitudinal anvil slot (234) or lower surface of lower jaw (212), respectively, thereby inhibiting suitable movement due to an undesirable amount of frictional braking force.

With movement of driving assembly (164) or firing beam (216) being undesirably inhibited, robotic surgical system (10) may need to (A) power robotic motor(s) (304, 306) past a predetermined maximum power output level for a specific instrument (110) in order to move driving assembly (164) or firing beam (216), or (B) use manual actuator (124) to manually "bailout" end effector (116, 210), in order to retract driving assembly (164) or firing beam (216) back toward a proximal position. Use of robotic motor(s) (304, 306) past a predetermined maximum power output level or use of manual actuator (124) to "bailout" instrument (110) may cause undesirable damage to instrument (110), thereby reducing the expected number of suitable uses of instrument (110), or even rendering instrument (110) unsuitable for further use.

Therefore, in some instances, it may be desirable to provide a robotic surgical system (10) that has robotic motor(s) (304, 306) that may utilize a motor control algorithm to increase the probability of proximally retracting firing beam (216) and/or other components of driving assembly (164) out of an undesirably stuck longitudinal position without having to power robotic motor(s) (304, 306) past a predetermined maximum power output level for a specific instrument (110); or without having to use manual actuator (124). Further, it may be desirable to utilize a motor control algorithm to increase the probability of overcoming an undesirably stuck longitudinal position and to further complete a firing process by distally actuating firing beam (216) and/or other components of driving assembly (164) in accordance with the description herein.

Figure 13:
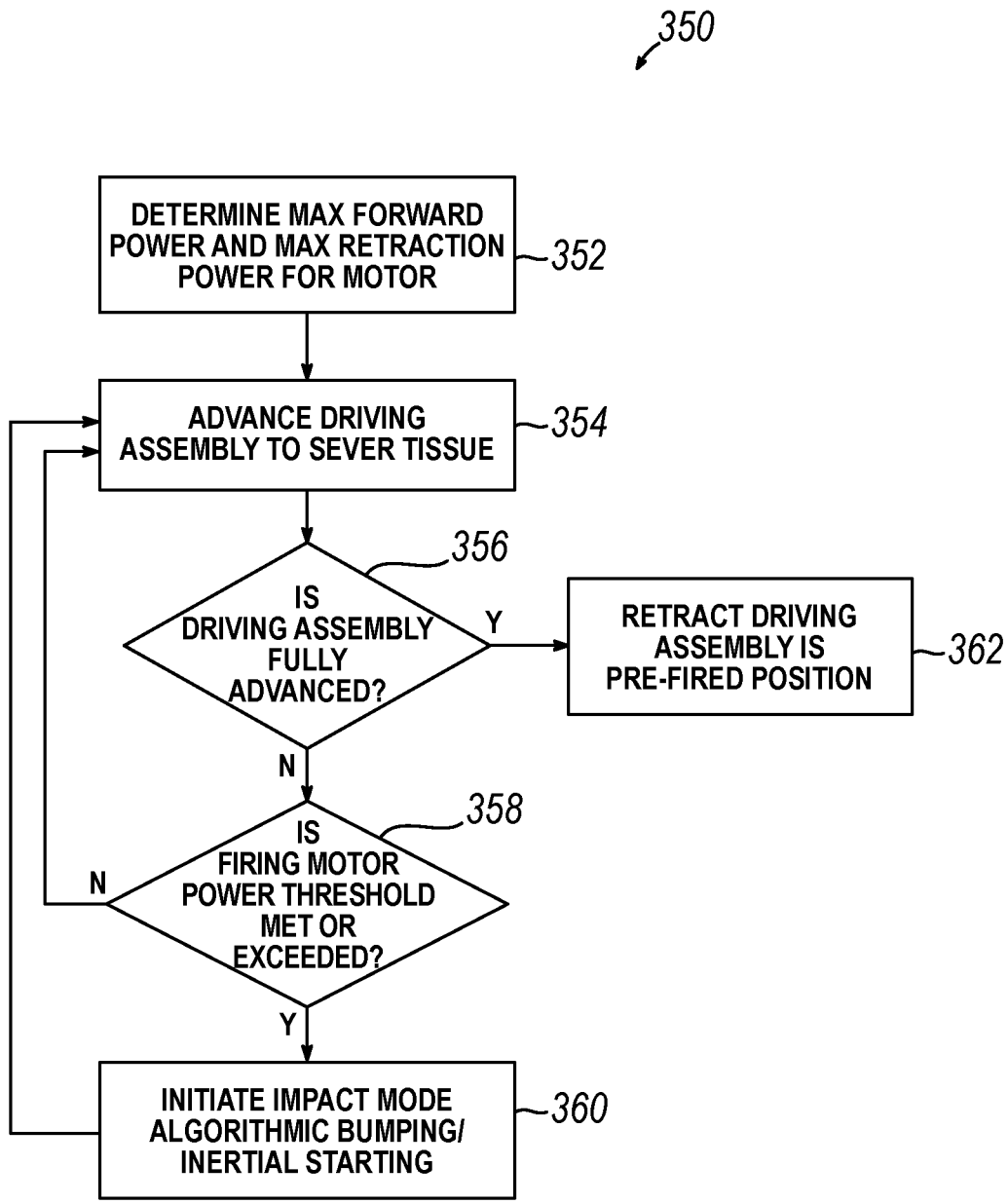
FIG. 13 depicts a block diagram of an exemplary impulse actuation motor control algorithm that may be used by the robotic arm and surgical instrument shown in FIG. 12.

FIG. 13 shows an exemplary impulse actuation motor control algorithm (350), while FIGS. 14A-14E show an exemplary use of algorithm (350). FIG. 15 shows a graph (400) representing the firing motor displacement (402) and the motor power consumption (404) over the time (406) elapsed during the exemplary use of algorithm (350) as shown in FIGS. 14A-14E. Exemplary impulse actuation motor control algorithm (350) may be utilized by robotic motors (304, 306), processing unit (308), and/or storage device (310) in order to increase the probability of retracting and/or fully firing end effector (116, 210) without having to (A) power robotic motor(s) (304, 306) past a predetermined maximum power output level for a specific instrument (110), or (B) use manual actuator (124).

In preparation of using robotic surgical system (10), a specific instrument (110) is coupled to robotic arm (342) such that processing unit (308) may establish various operational parameters for robotic arm (342) in controlling the specific instrument (110). Therefore, in the first step of algorithm (350), processing unit (308) may determine and establish maximum power output limits (352) for motors (304, 306) in actuating driving assembly (164)/firing beam (216) in accordance with the description herein.

Determining maximum power output limits (352) may include determining (A) a separate maximum power output level for motors (304, 306) to distally advance driving assembly (164)/firing beam (216) (i.e., a maximum forward power output level) and (B) a maximum power output level for motors (304, 306) to proximally retract driving assembly (164)/firing beam (216) (i.e., a maximum retraction power output level). In other words, motors (304, 306) may be limited to a first power output level to fire staples and sever tissue, while motors (304, 306) may be limited to a second power output level to proximally retract driving assembly (164)/firing beam (216).

In some instances, determining maximum power output limits (352) may be relatively simple, such as basing power output limits (352) on the type of instrument (110) being coupled to robotic arm (342). In other instances, processing unit (308) may determine the motor power output limits (352) for a specific instrument (110) based on various data accumulated throughout the life of the specific instrument (110) in use. Processing unit (308) may determine the motor power output limits (352) utilizing any suitable methods that would be apparent to one skilled in the art in view of the teachings herein, including the methods described herein. As mentioned above, processing unit (308) and storage device (310) may store specific data related to the prior use of a specific instrument (110). In such instances, processing unit (308) and storage device (310) (A) may store how many times a specific instrument (110) has been fully fired in accordance with the teachings herein, and/or (B) may store other suitable noteworthy events experienced by instrument (110) during exemplary use.

Figure 14A:
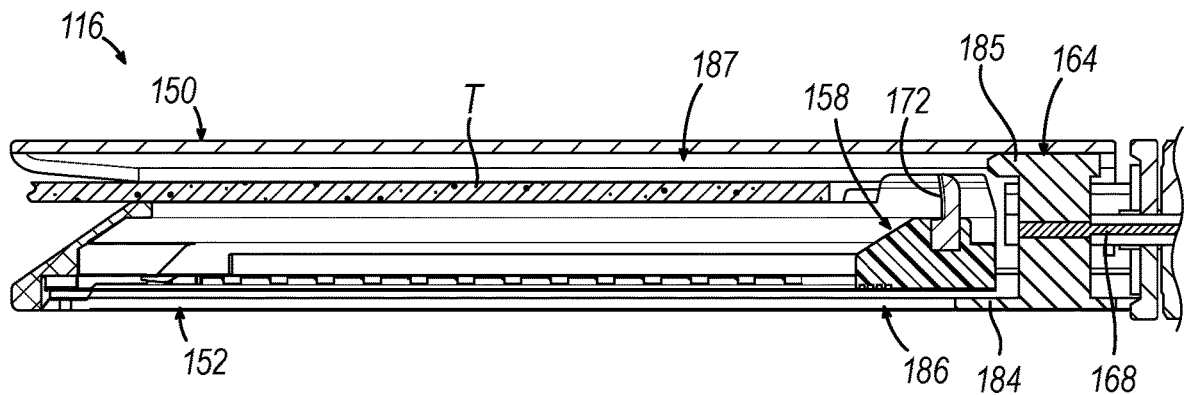
FIG. 14A depicts a cross-sectional side view of the end effector of FIG. 4, taken along a centerline thereof, in a pre-fired position.
Figure 14B:
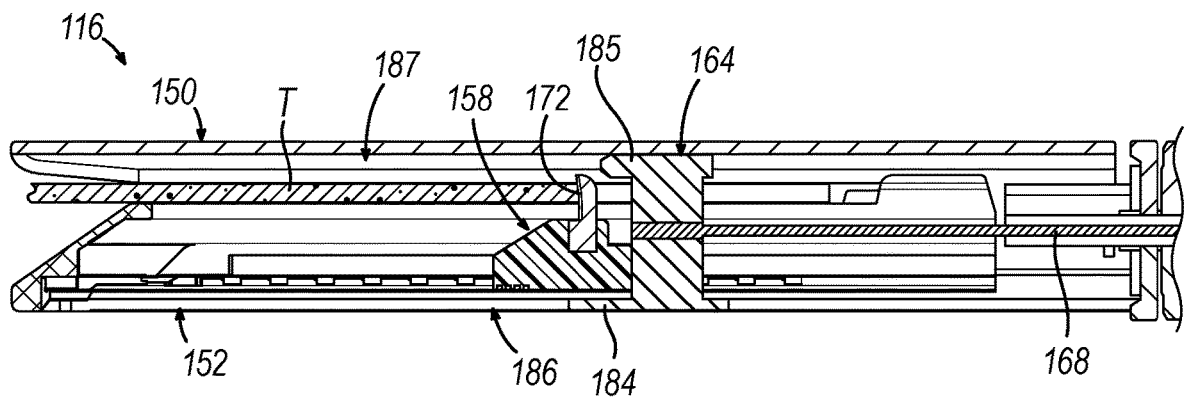
FIG. 14B depicts a cross-sectional side view of the end effector of FIG. 4, taken along a centerline thereof, in a partially fired position.
Figure 14C:
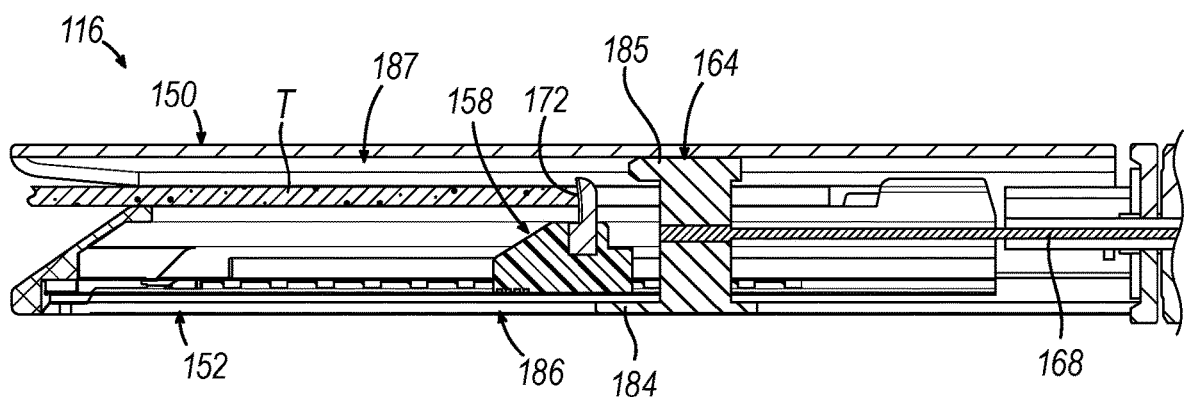
FIG. 14C depicts a cross-sectional side view of the end effector of FIG. 4, taken along a centerline thereof, with a driving assembly of the end effector partially retracted from the position shown in FIG. 14B.
Figure 15:
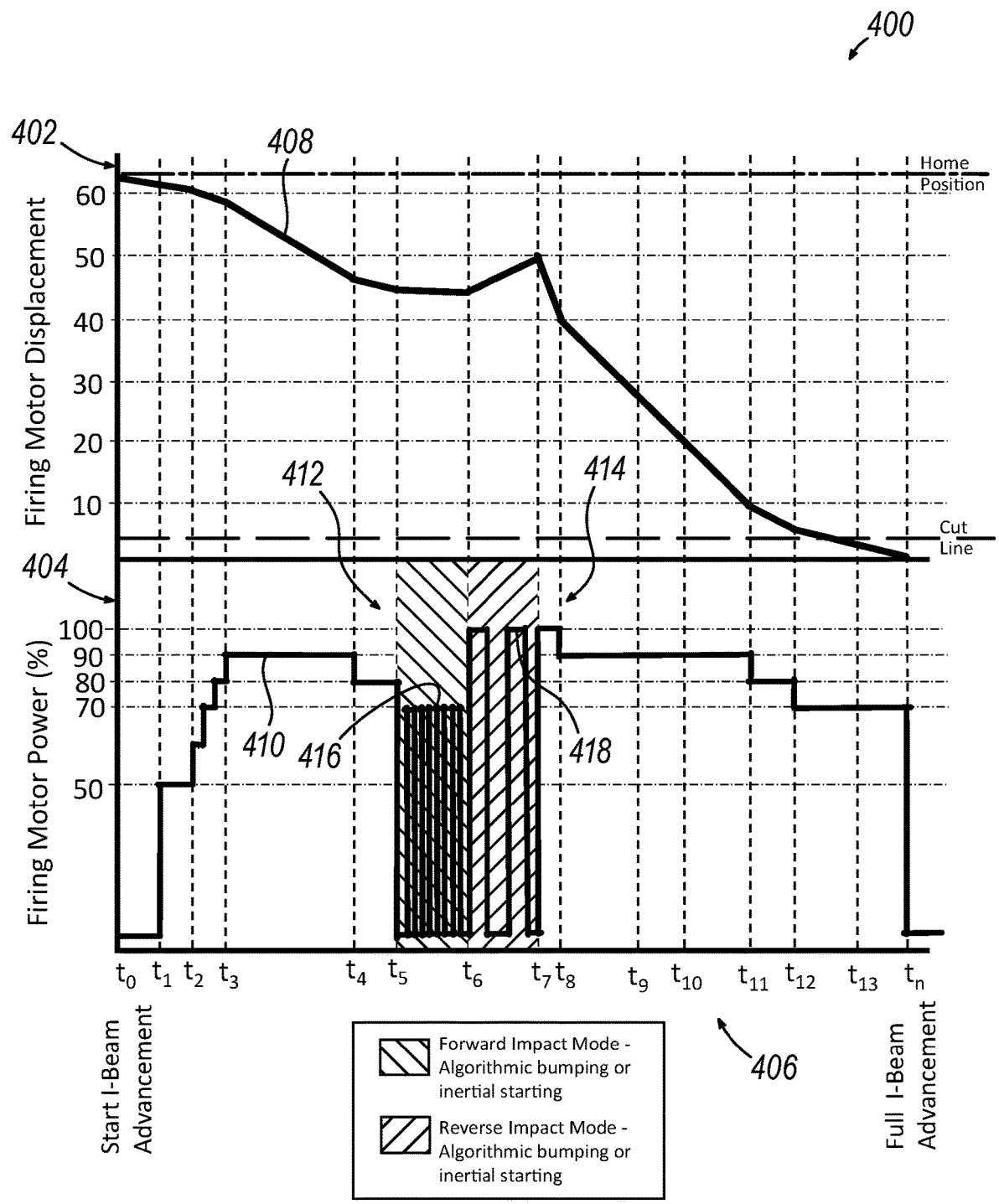
FIG. 15 depicts a graph representing the firing displacement and the firing motor power represented over time of the firing sequence shown in FIGS. 14A-14E.

With instrument (110) suitably coupled to robotic arm (342), an operator may utilize input control devices (36) of surgeon's console (16) to manipulate end effector (116) in grasping tissue (T) of a patient, as shown in FIG. 14A. It should be understood that at the moment shown in FIG. 14A, an operator may not have initiated the firing sequence for end effector (116) to sever and staple tissue (T). This moment may be represented at time (t0) on graph (400) shown in FIG. 15. Therefore, at the moment shown at time (t0), the firing motor displacement line (408) (which represents the longitudinal position of driving assembly (164) during the firing process) is shown at a position corresponding to driving assembly (164) being in a proximal pre-fired position, while power output line (410) (which represents the power output of motor (304, 306) actuating driving assembly (164)) is shown at a position corresponding to little or no power output for the motor (304, 306) configured to actuate driving assembly (164).

Once the operator is ready to sever and staple tissue (T) grasped between jaws (150, 152) of end effector (116), the operator may initiate the firing sequence via surgeon's console (16), which in turn causes processing unit (308) to instruct motor (304, 306) to distally advance driving assembly (354), as shown in control algorithm (350) of FIG. 13. Therefore, as shown between FIGS. 14A-14B, driving assembly (164) may advance distally, which in turn drives firing assembly (158) distally to sever and staple tissue (T) in accordance with the description herein. This movement may be respected between time (t0) and time (t4). Therefore, the firing motor displacement line (408) is shown to move at a slope corresponding to driving assembly (164) being distally advanced, while the power output line (410) is shown to increase up to 90% of motor's (304, 306) maximum power output.

Turning back to FIG. 13, while driving assembly (164) is being distally advanced (352), processing unit (308) may be running through selected portions of control algorithm (350) in order to determine whether or not driving assembly (164) is undesirably stuck (i.e., inhibited from movement to a greater degree than preferred). In the current example, processing unit (308) monitors if driving assembly (164) is fully advanced (356) to the post-fired position. If the firing process is complete without driving assembly (164) becoming undesirably stuck, processing unit (308) may instruct motor (304, 306) to retracted driving assembly (164) to the pre-fired position (362) shown in FIG. 14A.

In the current example, processing unit (308) may monitor the power output (410) of motor (304, 306) to determine if the power output (410) exceeds the predetermined power output limit (358) established earlier.

As shown in FIG. 15 between time (t3) and time (t4), if the power output (410) of motor (304, 306) reaches its maximum power output during normal operating use (in this case, 90% of maximum output) while motor displacement (408) is indicative of driving assembly (164) being distally advanced at a suitable rate of travel, processing unit (308) may continue to distally advance (354) driving assembly (164). However, as shown between time (t4) and time (t5) in FIG. 15 (which correlates with the position of driving assembly (164) shown in FIG. 14B), if motor displacement line (408) is indicative of driving assembly (164) resisting distal advancement (i.e., driving assembly (164) is not advancing distally as a suitable rate of travel), this may be indicative of driving assembly (164) being undesirably stuck in a longitudinal position. Therefore, processing unit (308) may initiate impact mode algorithmic bumping (360) in order to help driving assembly (164) become unstuck. Processing unit (308) may also initiate impact mode algorithmic bumping (360) in response to power output (410) of motor (304, 306) exceeding a predetermined power output limit (358). Any other suitable monitoring condition may be used in order to trigger initiation of impact mode algorithmic bumping (360) as would be apparent to one skilled in the art in view of the teachings herein.

In the current example, as shown in FIG. 15, algorithmic bumping (360) may involve a forward impact mode (412) (shown between times (t5) and (t6)) followed by a reverse impact mode (414) (shown between times (t6) and (t7)). In some instances, algorithmic bumping (360) may include only forward impact mode (412), only reverse impact mode (414), reverse impact mode (414) followed by forward impact mode (412), or multiple alternations between forward and reverse impact modes (412, 414). In some instances, algorithmic bumping (360) may automatically stop once processing device (308) determines driving assembly (164) is no longer undesirably stuck. In some instances, algorithmic bumping (360) may complete its predetermined cycle regardless of whether driving assembly (164) becomes unstuck during the bumping (360) process.

Forward impact mode (412) may include processing unit (308) instructing motor (304, 306) to activate at a power output (410) that fluctuates between little or no power output to a maximum forward impact power output (416) at a first frequency. In the current example, this fluctuation occurs in the substantial shape of a step-function. It should be understood that in forward impact mode (412), power output (410) of motor (304, 306) actuates driving member (164) in a distal direction. While in forward impact mode (412), sudden fluctuations of motor output (410) between no power output and maximum forward impact power output (416) may provide a jerk, jolt, shake, spasm, and/or bump-type reaction, leading to multiple impact-like starting and stopping of distal advancement of a driving member, also referred to as driving assembly (164). This impact-like motion may allow for driving member (164) to no longer be longitudinally stuck, thereby allowing the firing process to complete, along with retraction.

Reverse impact mode (414) may include processing unit (308) instructing motor (304, 306) to activate at a power output (410) that fluctuates between little or no power output to a maximum reverse impact power output (418) at a second frequency that is different than the first frequency of forward impact mode (412). Additionally, in the current example, maximum reverse impact power output (418) is greater than maximum forward impact power output (416).

In the current example, this fluctuation occurs in the substantial shape of a step-function. It should be understood that in reverse impact mode (414), power output (410) of motor (404, 406) actuates driving member (164) in a proximal direction toward the pre-fired position. This impact-like motion may cause driving assembly (164) to actuate from the position shown in FIG. 14B toward the position shown in FIG. 14C. While in reverse impact mode (414), sudden fluctuations of motor output (410) between no power output and maximum reverse impact power output (418) may provide a jerk, jolt, shake, spasm, and/or bump-type reaction, leading to multiple impact-like starting and stopping of proximal retraction of driving member (164). This impact-like motion may allow for driving member (164) to no longer be longitudinally stuck, thereby allowing the firing process to complete, along with retraction.

The difference in frequency and magnitude between forward and reverse impact mode (412, 414) may allow driving assembly (164) to have inertial starting and stopping (i.e., jerking, jolting, shaking, spasming, bumping) may increase the chances of driving assembly (164) becoming unstuck in the even one frequency and magnitude is not sufficient free driving assembly (164) from a stuck position.

Figure 14D:
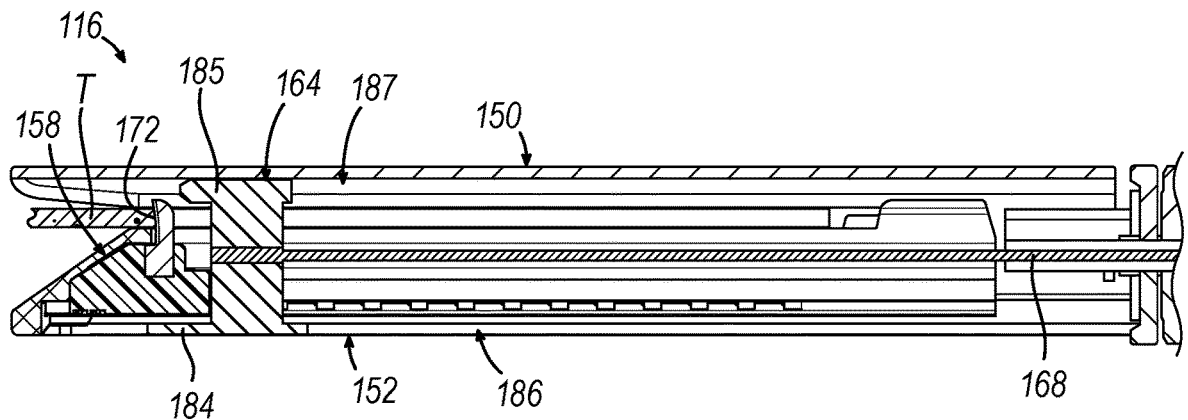
FIG. 14D depicts a cross-sectional side view of the end effector of FIG. 4, taken along a centerline thereof, with the end effector completely fired and the driving assembly of FIG. 14C in a distal position.
Figure 14E:
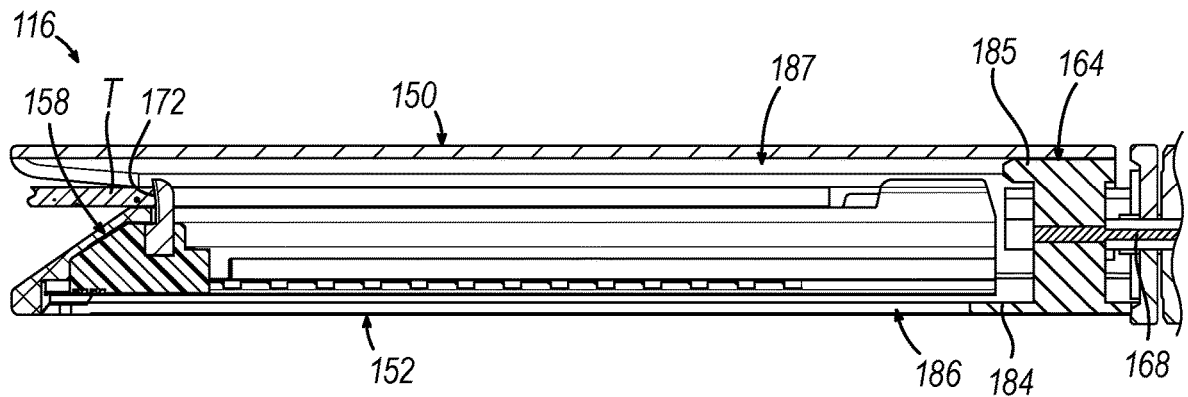
FIG. 14E depicts a cross-sectional side view of the end effector of FIG. 4, taken along a centerline thereof, with the end effector completely fired and the driving assembly of FIG. 14C retracted toward the pre-fired position.

Once the impact mode (360) is complete, processing unit (308) will then loop back to advancing (354) driving assembly (164) until driving assembly (164) is fully advanced, as shown in FIG. 14D. Once fully advanced, processing unit (308) may then instruct motor (304, 306) to retract driving assembly (164) back to the proximal, pre-fired position. It should be understood that impact mode (360) may be initiated if driving assembly (164) becomes stuck while being proximally retracted to the pre-fired position after completing the firing process. It should be understood that processing unit (308) may initiate impact mode (360) more than one time if needed.

Once the firing process is complete, the operator may remove instrument (110) from the surgical site, remove instrument (110) from robotic arm (342), and reprocess instrument (110) for another firing, if desired. It should be understood that while int eh current example, end effector (116) was used, end effector (210) may be used in replacement of end effector (116).

While in the current example, processing unit (308) monitors both the rate of travel which driving assembly (164) is advanced distally and the power output (410) to determine whether or not to initiate algorithmic bumping (360), this is merely optional. In some instances, processing unit (308) may just monitor the rate of travel at which driving assembly (164) is being distally advanced to determine whether or not to initiate algorithmic bumping (360). In other instances, processing unit (308) may just monitor power output (410) to determine whether or not to initiate algorithmic bumping (360). In other instances, processing unit (308) may measure to resistance force imparted on any suitable position of firing assembly (158) or driving assembly (164) in order to determine whether or not to initiate algorithmic bumping (360).

It should be understood that processing unit (308) may read all the data produced by motor (304, 306) and shown in graph (400) in real time and utilize such data to execute algorithm (350) described herein.

While in the current example, algorithmic bumping (360) is initiated based off of driving assembly (164) resisting distal advancement and/or power output (410) of motor (304, 306) exceeding a predetermined threshold, any other suitable responses may be utilized based on any other suitable motor control input as would be apparent to one having ordinary skill in the art in view of the teachings herein. For example, the clamping time/force at which end effector (116) grasps tissue could be modified based off rate of travel at which driving assembly (164) is distally advanced and/or the predetermined power output threshold of motor (304, 306). As another example, the rate of travel at which driving assembly (164) is distally advanced and/or the predetermined power output threshold of motor (304, 306) could be modified based on the number of clamping attempts required for end effector (116) to suitably grasp tissue. As another example, the rate of travel at which driving assembly (164) is distally advanced and/or the predetermined power output threshold of motor (304, 306) could be modified based on the thickness of tissue being grasped by end effector (116). As another example, the rate of travel at which driving assembly (164) is distally advanced and/or the predetermined power output threshold of motor (304, 306) could be modified based on the type of staple cartridge loaded on end effector (116). As another example, the rate of travel at which driving assembly (164) is distally advanced and/or the predetermined power output threshold of motor (304, 306) could be modified based on the number of pauses or the cumulative duration of pauses which driving assembly (164) experiences during distal advancement in order to staple and sever tissue in accordance with the description herein.

B. Exemplary Motor Control Algorithm for Determining Maximum Motor Power Output Levels for a Firing Assembly of Specific Instruments As mentioned above, when a specific instrument (110) initially couples with a robotic arm (342), it may be desirable to determine a maximum forward power and a maximum retraction power for motors (304, 306) to actuate driving assembly (164)/firing beam (216) in order to staple and sever tissue in accordance with the description herein. Further, it may be desirable to utilize a motor control algorithm that adjusts the power output levels which motor(s) (304, 306) may operate at based on the number of uses and other noteworthy events experienced by a specific instrument (110). Modifying the power output levels which motor (304, 306) may operate a specific instrument (110) during the life of the specific instrument (110) may reduce the chances of mechanical failure of certain components of instrument (110)

Figure 16:
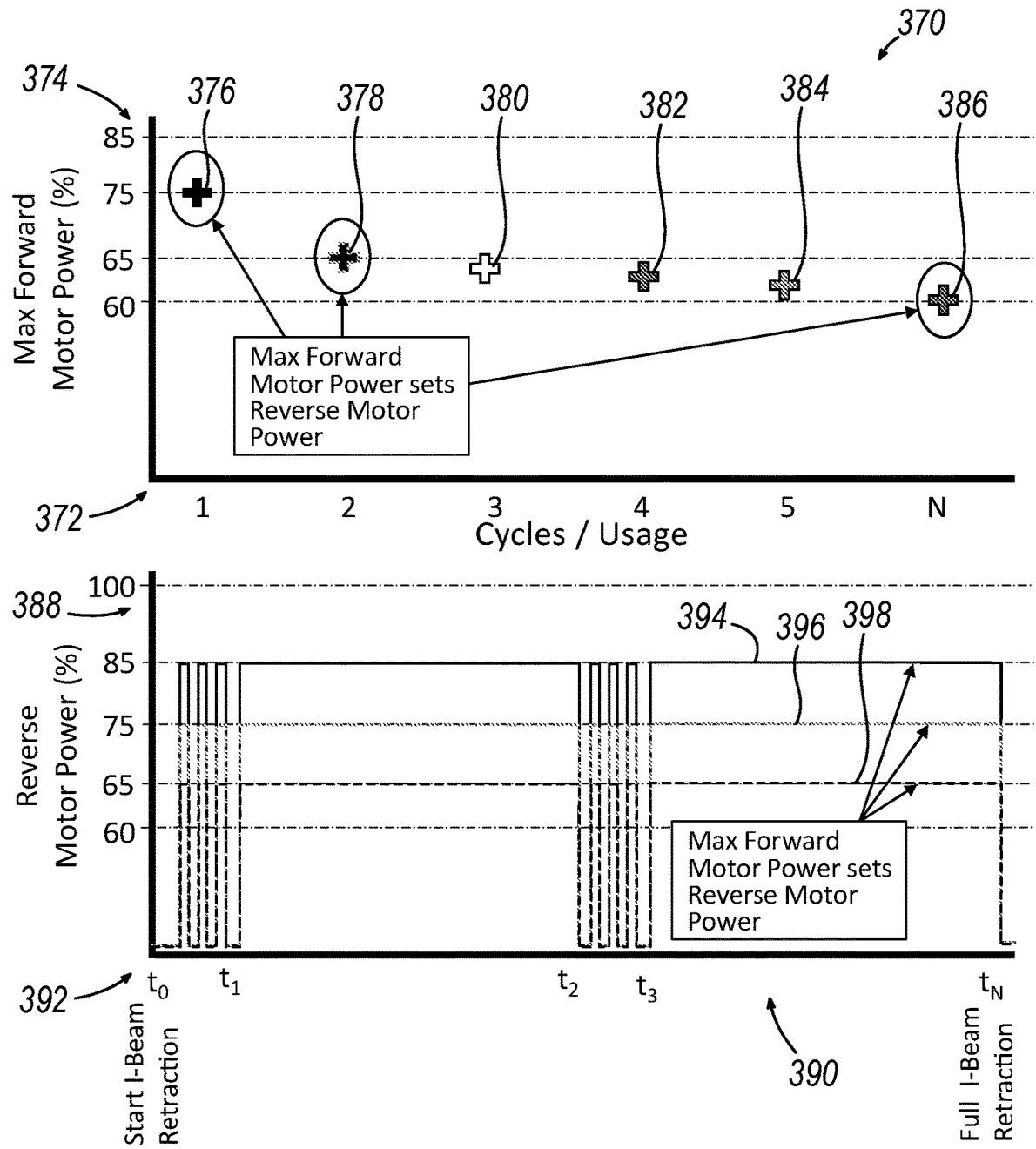
FIG. 16 depicts a graph representing the maximum forward and reverse motor power represented over the usage cycle and time, respectively.

FIG. 16 shows a first graph (370) representing the cycles which instrument has been used compared to maximum forward power output level motors (304, 306) may be utilized to distally actuate driving assembly (164) or firing beam (216). Processing unit (308) may recall a cycles/usage information (372) once a specific instrument (110) is coupled to robotic arm (342) to determine what the maximum forward power value (374) motor (304, 306) may operate during exemplary use. Therefore, the number of cycles in which a specific instrument (110) is used may be utilized in determining the maximum forward power value (374) at which motors (304, 306) may operate.

It should be understood that once a specific instrument (110) is used to fire staples and sever tissue in accord with the description herein, processing unit (308) may add a cycle/usage to storage device (310) for the specific instrument (110). Therefore, once the specific instrument (110) is reprocessed and recoupled with robotic arm (342) for additional use, processing unit (308) will then determine instrument (110) has been used one more time compared to the previous use and will therefore adjust the maximum motor power limits (352) for operating the specific instrument (110) accordingly.

The maximum forward power value (374) represents the maximum power output level motor (304, 306) may operate to distally advance driving assembly (164) or firing beam (216) to sever and staple tissue in accordance with the teachings herein. Processing unit (308) may then utilize the determined maximum forward power value (374) in order to determine a maximum reverse power value. The maximum reverse power value represents the maximum power output level motor (304, 306) may operate at while proximally retracting driving assembly (164) or firing beam (216) in accordance with the teachings herein. In some instances, the maximum reverse power value may be determined by the number of cycles a specific instrument (110) has been used, and the maximum forward power value may be determined based off the maximum reverse power value.

In the current example, as shown in FIG. 16, processing unit (308) would determine the maximum forward motor power used for a specific instrument (110) during its first cycle/use (376) to be 75% of the maximum power production of motor (304, 306). During the second cycle (378), third cycle (380), fourth cycle (382), fifth cycle (384), and $n^{th}$ cycle (386), the maximum power capable of being achieved by motor (304, 306) may drop to 65%, 64%, 63%, 62%, and 61%, respectively, of the maximum power production of motor (304, 306). In the current example, the maximum forward power production of motors (304, 306) during the first cycle (376) may be substantially greater than the sequential cycles. This greater drop after the first use may be due to break-in and/or initial wear of components of end effector (116, 210) after the first use.

Based on the information of the maximum forward motor power in the current example, as shown in the firing assembly retraction graph (388), the maximum reverse motor power would be 85%, 75%, and 65% of the maximum power production of motor (304, 306) for the first cycle (394), second cycle (396), and third cycle (398), respectively. In some instances, the maximum reverse motor power output level would not be allowed to surpass a defined amount over the maximum forward motor power output level. In the current example, that power difference margin would be 10%.

In the current example, the maximum forward and reverse motor power output levels are reduced as the number of cycles/usages increase for each specific instrument (110). This reduction in the forward motor power output level may be proportionate to the wear of the pusher member (166), pusher block (236), jaws (150, 152, 212, 214) and the channels defined by jaws due to the frictional engagement between respective components during exemplary firing of staples and severing of tissue. This wear due the exemplary use may lead to a reduction in lubrication as well as surface finish of metal components, thereby increasing the frictional resistance to distal advancement of driving assembly (164) or firing beam (216). The lowering of the maximum forward and reverse motor power output levels may help ensure motors (304, 306) do not accidentally break internal components of instrument (110) during exemplary use, as breaking such internal components may increase the difficulty of retracting driving assembly (164) or firing beam (216) in accordance with the description herein.

In the current example, the maximum reverse motor power is greater than the corresponding maximum forward motor power. This difference in maximum motor power may help ensure that driving assembly (164) or firing beam (216) may be retracted proximally if they become undesirably stuck in a longitudinal position during distal advancement with a maximum forward motor power output level in accordance with the description herein.

While in the current example, the maximum motor power output levels may be determined by the number of cycles a specific instrument (110) is used, any other suitable factor may be used to determine the maximum motor power output levels as would be apparent to one skilled in the art in view of the teachings herein. For instances, a calculation based on an accumulated number of noteworthy events, as described in greater detail below, may be used to determine the maximum motor power levers for a specific instrument (110) during a specific cycle of use.

C. Exemplary Motor Control Algorithm Utilizing Multiple Robotic Motors Cooperatively As mentioned above, during exemplary use of end effector (210), distal advancement of closure tube (not shown) and closure ring (230) (see FIGS. 10 and 22A-22E) are used to close end effector (210). In other words, distal advancement of closure tube (not shown) and closure ring (230) are used to move lower jaw (212) and anvil jaw (214) toward each other in order to grasp tissue in accordance with the description herein. As also mentioned above, with tissue grasped between staple cartridge (218) and anvil jaw (214), firing beam (216) may then be advanced distally in order to sever and staple tissue in accordance with the description herein.

Figure 17:
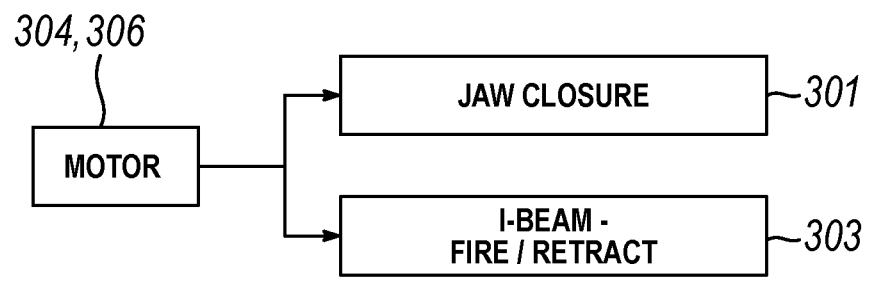
FIG. 17 depicts a schematic view of a motor assembly of the robotic arm of FIG. 12 coupled with the jaw closure assembly and the firing assembly of the surgical instrument of FIG. 4.

As schematically shown in FIG. 17, it should be understood that jaw closure assembly (301), which includes closure tube (not shown), closure ring (230), and respective intermediary components, may be in communication with a first robotic motor (304) via respective output coupler (300) and input coupler (130); while a firing assembly (303), which includes firing beam (216), and respective intermediary components, may be in communication with a second robotic motor (306) via respective output coupler (302) and input coupler (130). In other words, end effector (210) may be configured such that movement of jaws (212, 214) in order to grasp tissue may be performed independently with respect to actuation of firing beam (216) in order to sever and staple grasped tissue.

As mentioned above, while end effector (210) is used to staple and sever grasped tissue, distal advancement of firing beam (216) (see FIGS. 11 and 20A-20E) may be inhibited such that robotic surgical system (10) may have to power robotic motor (304) past a predetermined maximum power output level in order to distally advance firing beam (216) further. In some instances, rather than using robot motor(s) past a predetermined power output level to further staple and sever grasped tissue is accordance with the description herein, robotic motor (306) may be programed to temporarily stop, stall, halt, or otherwise delay advancement of firing beam (216) for a predetermined amount of time once the predetermined maximum motor power output level for advancing firing beam (216) is reached. In such instances, the temporary delay of advancing firing beam (216) may act as a passive means of reducing the required firing force for robotic motor (306) to distally advance firing beam (216). This passive means of reducing the required firing force may allow for a "milking effect" to occur between jaws (212, 214) and grasped tissue, thereby reducing the amount of force required for firing beam (216) to staple and sever tissue in accordance with the teachings herein.

In some instances, instead of passively waiting for the "milking effect" to reduce the force required for robotic motor (306) to distally advance firing beam (216) without exceeding a predetermined power output level of robotic motor (306), it may be desirable to actively reduce the firing force required for robotic motor (306) to advance firing beam (216) to thereby prevent robotic motor (306) from operating past the predetermined power output level.

Figure 18:
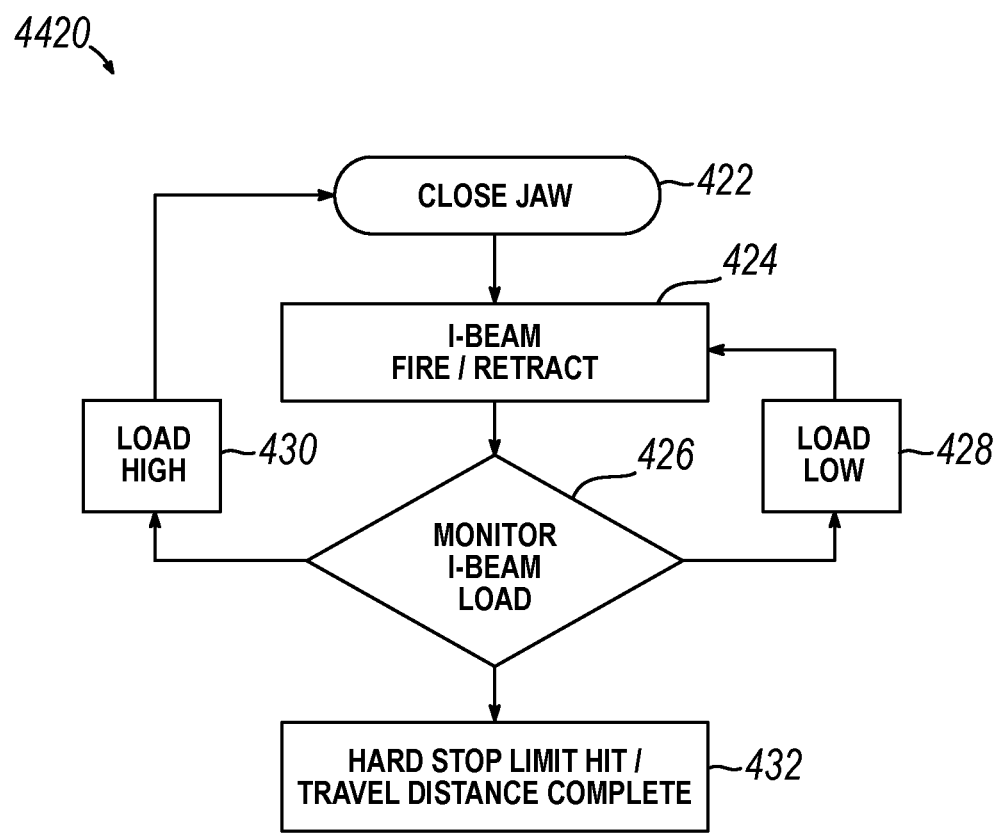
FIG. 18 depicts a block diagram of an exemplary motor control algorithm that may be used by the robotic arm and surgical instrument shown in FIG. 12.

FIG. 18 shows a motor control algorithm (420) may be utilized by robotic surgical system (10) in order to simultaneously or synchronously activate robotic motors (304, 306) that are in communication with jaw closure assembly (301) and firing assembly (303), respectively, thereby reducing the amount of firing force required to fully advance firing beam (216). FIGS. 20A-20E show an exemplary use of algorithm (420), while FIG. 21 shows a graph (440) representing the firing motor displacement (444), the motor power output (446) represented as a percentage, the closure motor force (448), and the firing motor force (450) over the time (442) elapsed during exemplary use of algorithm (420) as shown in FIGS. 20A-20E.

Figure 20A:
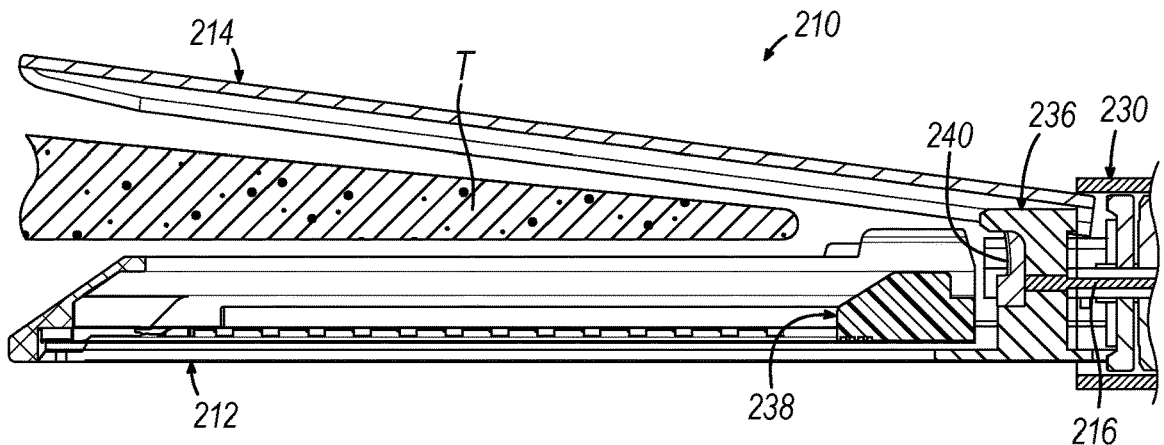
FIG. 20A depicts a cross-sectional side view of the end effector of FIG. 10, taken along a center line thereof, with the jaws in an open position and the firing assembly in a pre-fired position.
Figure 20B:
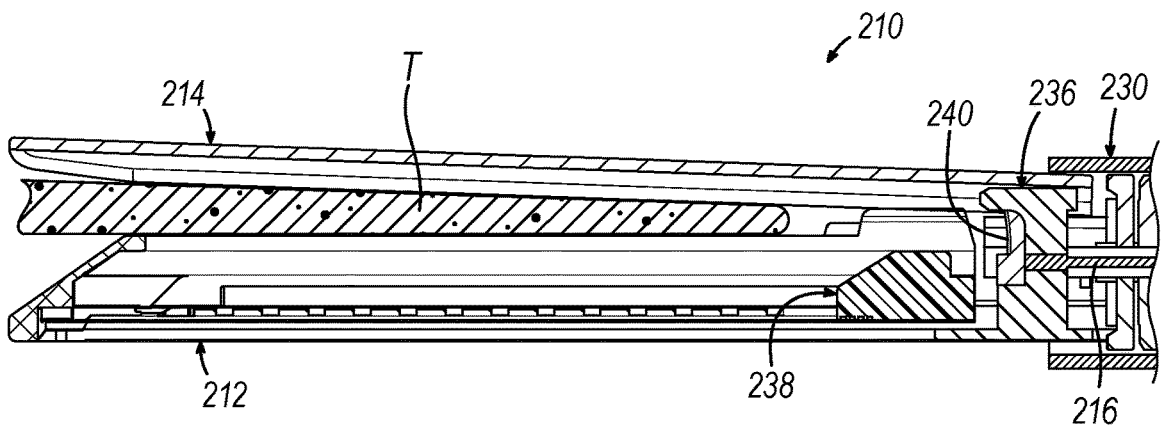
FIG. 20B depicts a cross-sectional side view of the end effector of FIG. 10, taken along a center line thereof, with the jaws in a first closed position and the firing assembly in the pre-fired position.

First, as shown between FIGS. 20A-20B, an operator may utilize input control devices (36) of surgeon's console (16) to manipulate end effector (210) in grasping tissue (T) of a patient. This may be represented as the initial jaw closure (422) in motor control algorithm (420) shown in FIG. 18.

Figure 21:
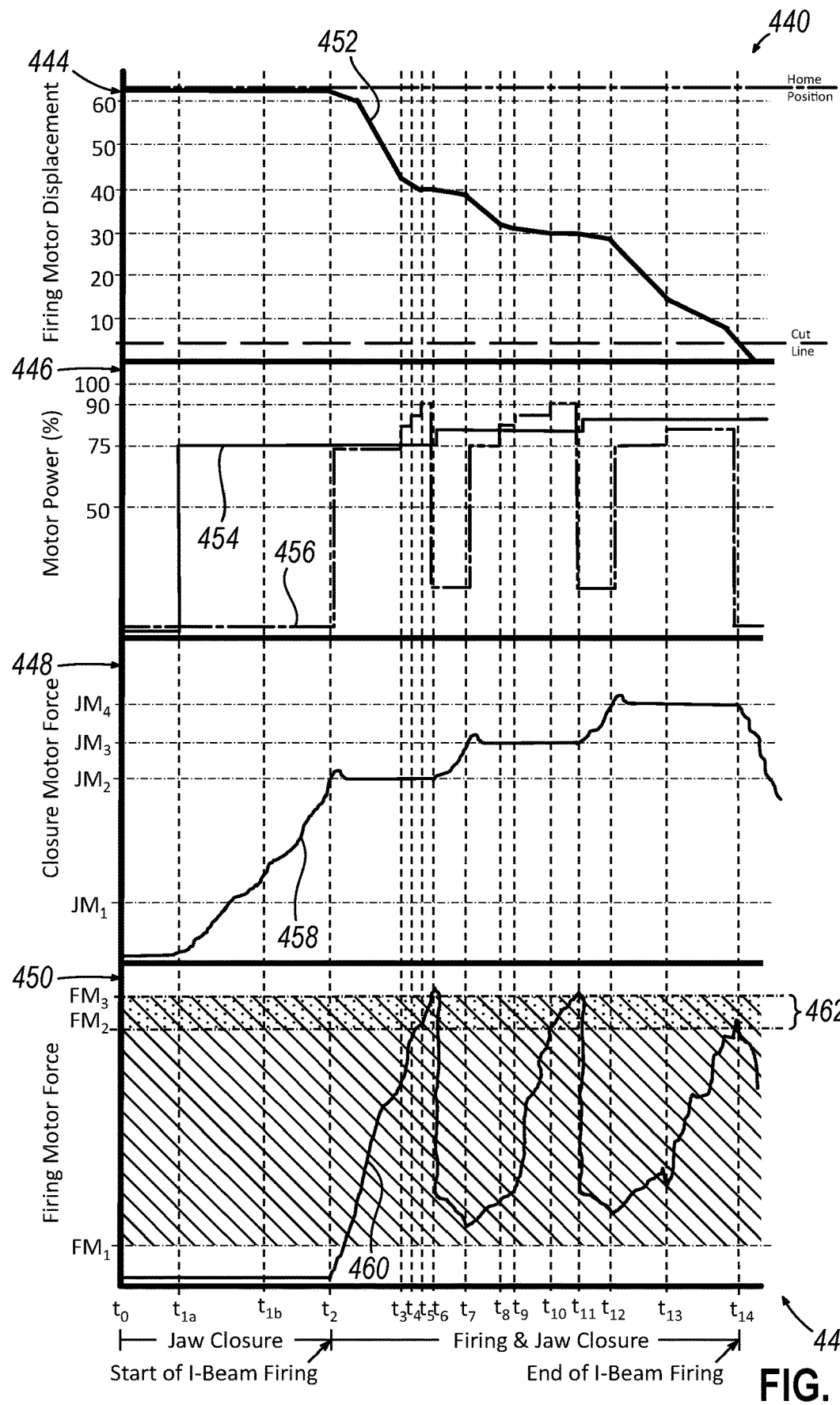
FIG. 21 depicts a graph showing the firing motor displacement, motor power, jaw closure force, and firing force over time of the firing sequence shown in FIGS. 20A-20E.

The initial closure of jaws (212, 214) to grasp tissue (T) is represented on graph (440) of FIG. 21 between time (t0) and time (t2). Since jaw closure assembly (301) and firing assembly (303) are operated by separate motors (304, 306), respectively, and since actuation of firing beam (216) has not yet happened, firing motor displacement line (452) (which represents the longitudinal position of pusher block (236)), firing motor output line (456) (which represents output power of firing motor (306)) and the firing motor force line (460) (which represents the force imparted on firing motor (306) in order to drive firing beam (216)) remain relatively unchanged between times (t0) and (t2).

However, the closure motor power output line (454) (which may represent output power of closing motor (304)) raises from little or no power output up to 75% in the current example in order to manipulate jaws (212, 214) to grasp tissue (T). Additionally, the closure motor force line (458) (which represents the force imparted on closing motor (304) in order to drive jaws (212, 214) closer together to grasp tissue (T)) increases to JM2 in response to motor (304) driving jaws (212, 214) to grasp tissue (T). Therefore, closure motor (304) is activated to drive jaws (212, 214) such that the reactive closure motor force line (458) gradually increases due to contact between grasped tissue (T) and jaws (212, 214).

Figure 20C:
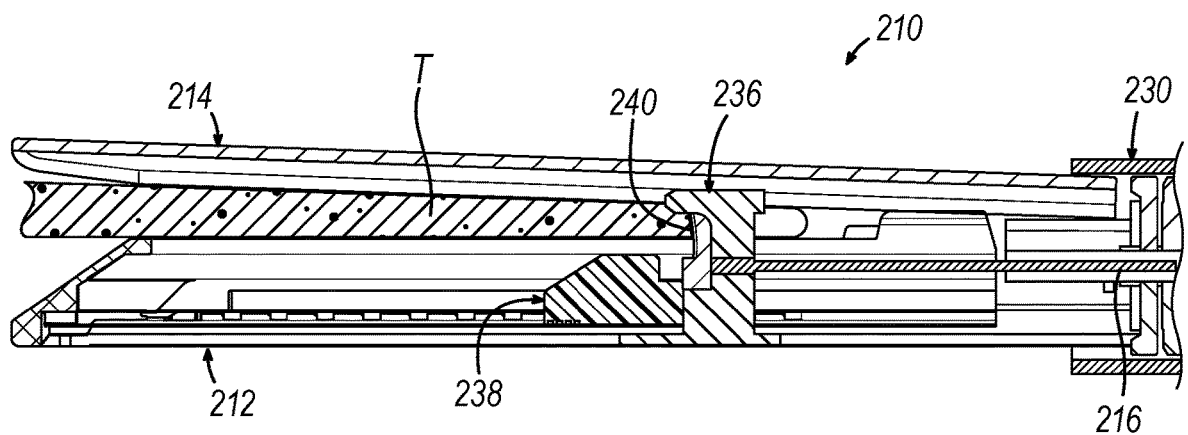
FIG. 20C depicts a cross-sectional side view of the end effector of FIG. 10, taken along a center line thereof, with the jaws in the first closed position and the firing assembly in the partially fired position.

When the operator is ready to sever and staple tissue (T) grasped between jaws (212, 214) of end effector (210), the operator may initiate the firing sequence via surgeon's console (16), which in turn may initiate processing unit (308) to instruct firing motor (306) to advance (424) (see FIG. 18) firing beam (216) as shown between FIGS. 20B-20C. The initial advancement of firing beam (216) to staple and sever tissue (T) is represented on graph (440) of FIG. 21 between time (t2) and time (t6).

Since jaw closure assembly (301) has not been substantially moved between times (t2) and (t6), the jaw motor force line (458) and the closure motor power output line (454) remain relatively unchanged between times (t2) and (t6). However, the firing motor power output line (456) raises from little or no power output up to 75% initially, and then further to 90% in the current example, in order to advance firing beam (216). Additionally, in response to motor (306) driving the firing beam (216) to staple and cut tissue (T), the firing motor force line (460) increases from substantially zero all the way to within a limit zone (462) defined by FM2 and FM3, Therefore, firing motor (306) is activated such that the firing motor force line (460) gradually increases due to firing beam (216) contacting both tissue (T) and wedge sled (238).

As shown in FIG. 18, control algorithm (420) includes monitoring (426) the load on firing beam (216) such that if the load is below (428) the trigger limit zone (462), processing unit (308) instructs firing motor (306) to further advance firing beam (216). However, if the measured load on firing beam (216) is measured as a high load (430) (i.e., within the limit zone (462) defined by FM2 and FM3) this may be indicative of robotic motor (304) operating past a predetermined maximum power output level, which may lead to undesirable consequences described above.

Figure 20D:
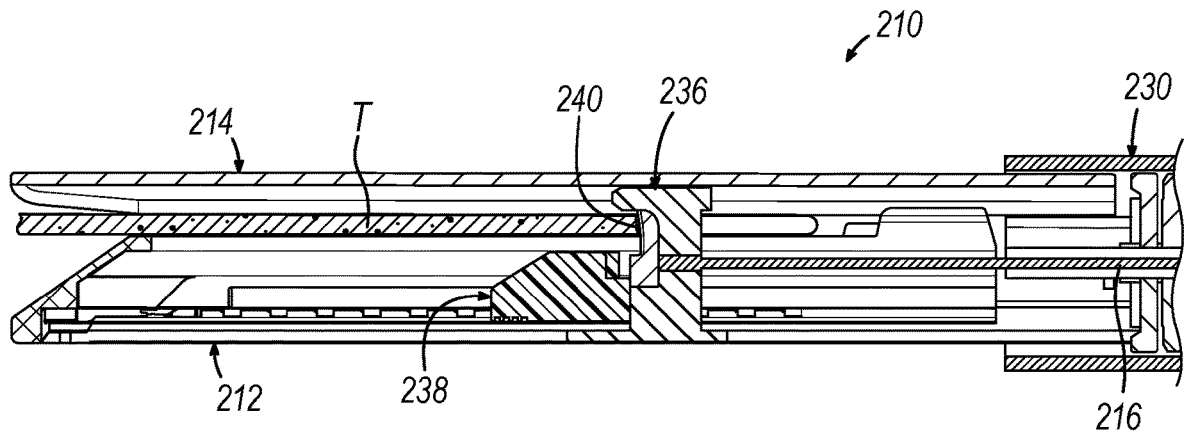
FIG. 20D depicts a cross-sectional side view of the end effector of FIG. 10, taken along a center line thereof, with the jaws in a second closed position and the firing assembly in the partially fired position.
Figure 20E:
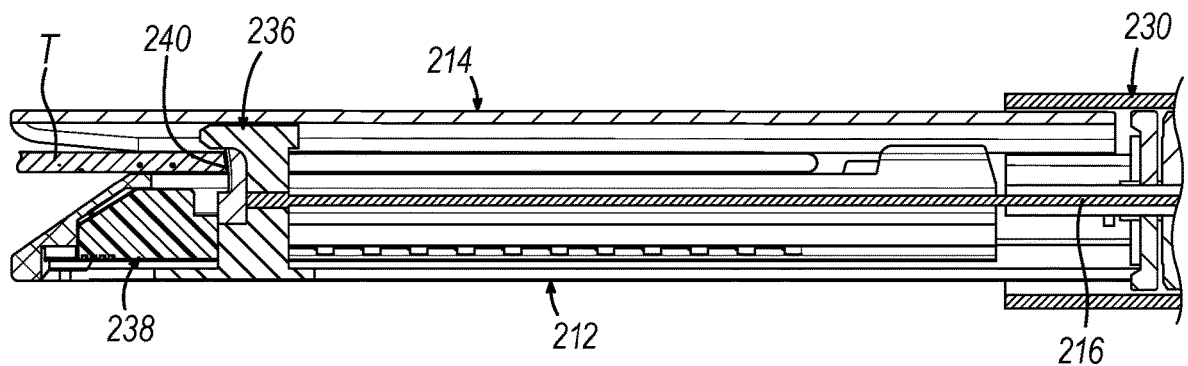
FIG. 20E depicts a cross-sectional side view of the end effector of FIG. 10, taken along a center line thereof, with the jaws in the second closed position and the firing assembly in the fired position.

Instead of passively waiting for the milking effect to reduce the amount of force required to distally advance firing beam (216) such that firing motor (306) is not forced to operate within limit zone (462), processing unit (308) instead instructs closing motor (304) to further close jaws (212, 214), as shown in FIG. 20D. Further closing jaws (212, 214) during the firing process may reduce the gap distance between jaws (212, 214), which in turn may actively reduce the firing force required to advance firing beam (216) such that firing motor (306) is not forced to operated past a predetermined maximum power output level.

Once the firing force required to advance firing beam (216) is sufficiently reduced, the processing unit (308) may then instruct firing motor (306) to distally advance (424) firing beam (216) to sever and staple tissue (T). If firing motor (306) experienced a firing force within limit zone (462) again, processing unit (308) may repeat the further closing of jaws (212, 214) to lower reduce the gap distance and firing forces required to actuate firing beam (216) until firing beam (216) reaches the fully fired position shown in FIG. 20E. One the fully fired position is achieved, processing unit (308) may instruct firing motor (306) to proximally retract firing beam (216).

As shown between times (t6) and (t7) in the graph (440) on FIG. 21, the further activation of closing motor (304) to reduce the gap distance occurs sequentially with the activation of firing motor (306) to drive firing beam (216). However, it should be understood that this is merely optional, as the activation of closing motor (3040 and the activation of firing motor (306) may occur simultaneously in order to actively reduce the gap distance while still stapling and severing tissue (T) in accordance with the description herein.

It should be understood this motor control algorithm (420) may be initiated during at any suitable time during the firing process as would be apparent to one skilled in the art in view of the teachings herein. It should also be understood that processing unit (308) may read all the data produced by motor (304, 306) and shown in graph (400) in real time and utilize such data to execute algorithm (350) described herein.

Figure 22A:
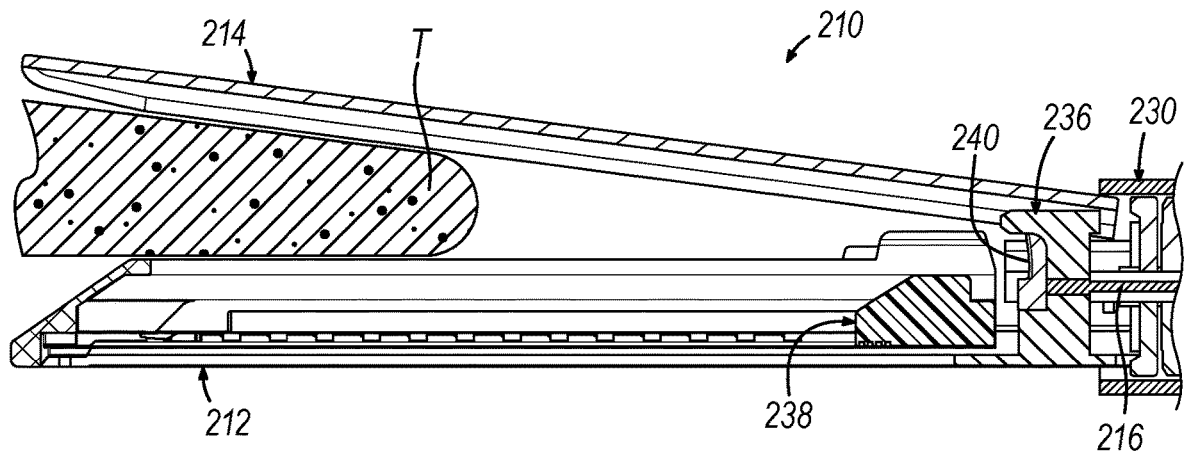
FIG. 22A depicts a cross-sectional side view of the end effector of FIG. 10, taken along a center line thereof, prior to grasping tissue along a first depth of the end effector.
Figure 22B:
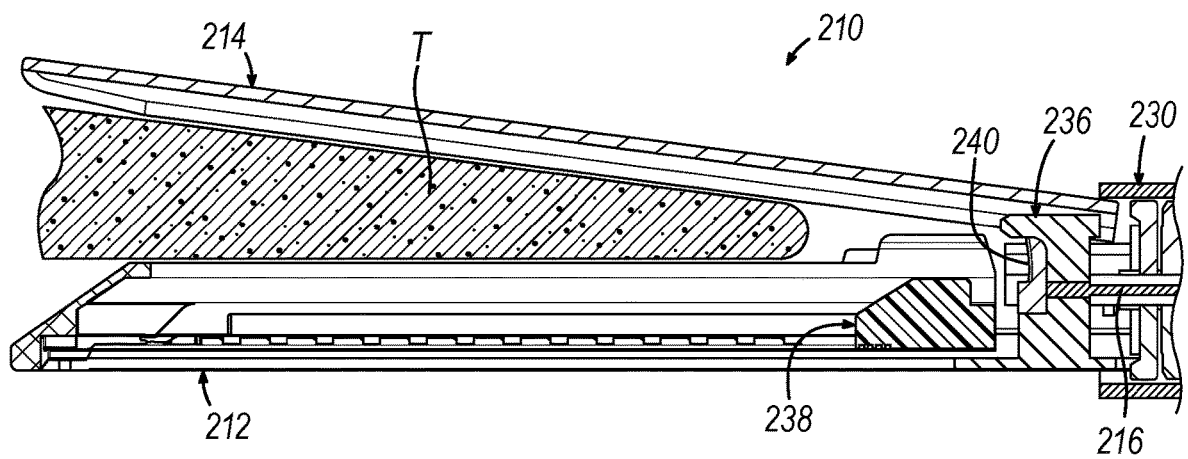
FIG. 22B depicts a cross-sectional side view of the end effector of FIG. 10, taken along a center line thereof, prior to grasping tissue along a second depth of the end effector that is shallower than the first depth shown in FIG. 20A.
Figure 23:
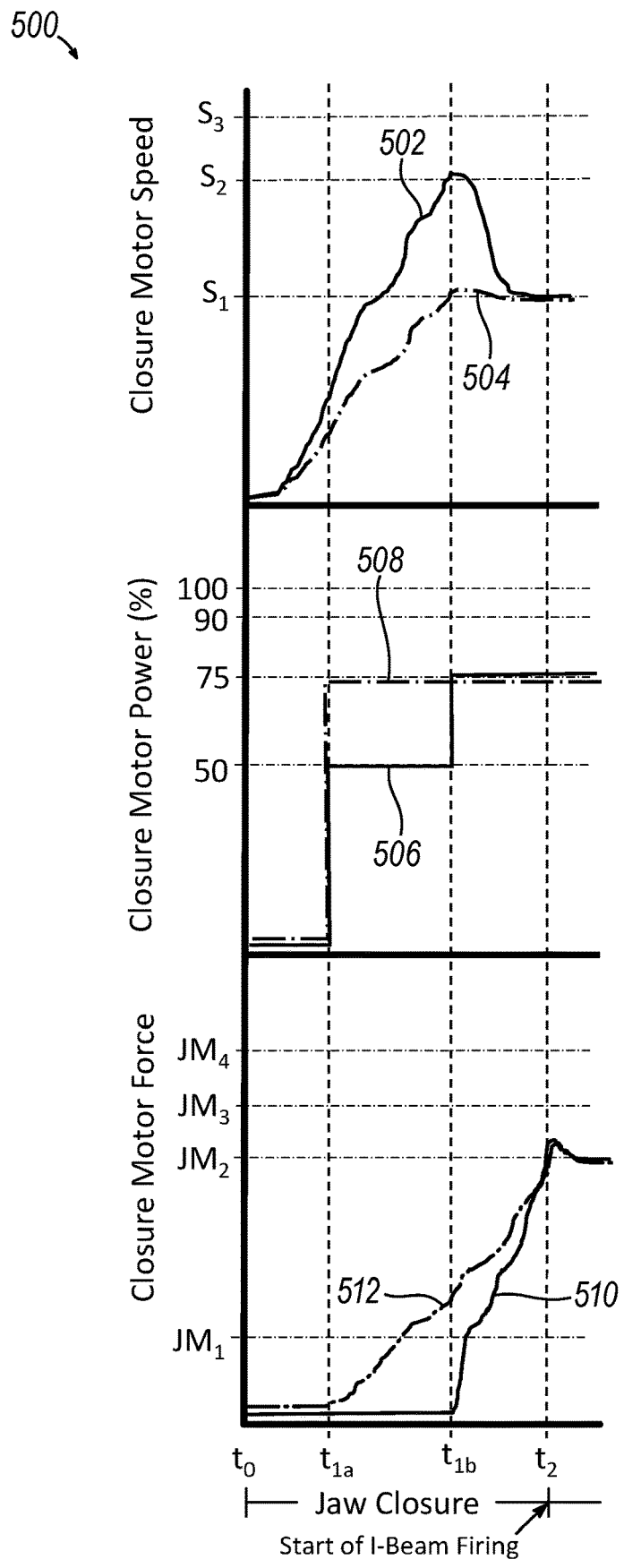
FIG. 23 depicts a graph showing closure motor speed, closure motor power, and closure motor force of the end effector of FIG. 10 grasping tissue at the positions shown in FIGS. 22A and 22B over time.

In some instances, as shown in FIGS. 22A-22B, tissue (T) may be grasped along different lengths of jaws (212, 214). For instances, FIG. 22A show tissue (T) being grasped at a proximal most end that is located halfway along jaws (212, 214), while FIG. 22B shows tissue (T) being grasped at a proximal most end that is located closer to the proximal end of jaws (212, 214). As can be seen in graph (500) of FIG. 23, the closure motor speed, the closure motor power, and the closure motor force are different for when tissue is grasped halfway along jaws (212, 214) (as represented by lines (502, 506, 510); as compared to when tissue (T) is fully grasped along the length of jaws (212, 214) (as represented by lines (504, 508, 512).

Figure 19:
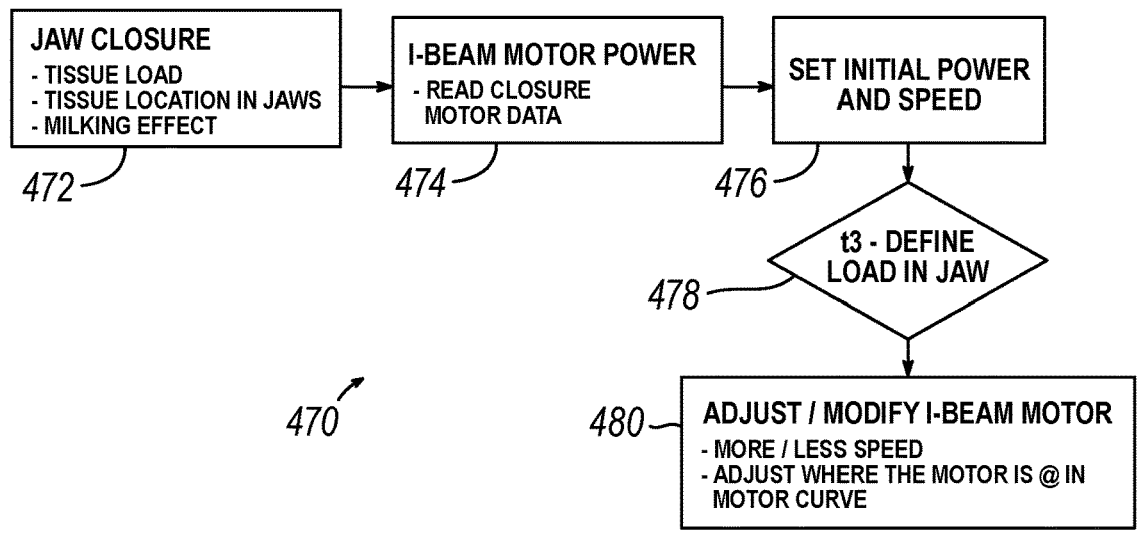
FIG. 19 depicts a block diagram of an exemplary motor control algorithm that may be used by the robotic arm and surgical instrument shown in FIG. 12.

As mentioned above, sensor assembly (312) may be configured to determine the location along jaws (212, 214) which tissue is grasped, the tissue load imparted on jaws (212, 214) from grasping tissue (T), etc. FIG. 19 shows an algorithm (470) that may be utilized after jaws (212, 214) grasp tissue (T) it order to establish the appropriate operating parameters. For instance, in block (472), once tissue is grasped, the sensor assembly (312) may communicate to processing unit (308) the tissue load, the location of tissue in jaws (212, 214), and whether any milking effect is being experienced. In block (474), processing unit (308) may further determine the motor operating parameters for firing beam (216) based on data received from closing motor (304) as well as the jaw closure data of block (472). With these parameters, processing unit (308) may instruct motors (304, 306) to close jaws (212, 214) and advance firing beam (216) at the determined power and speed based at least partially on recently obtained data, as shown in block (476). If the load in jaws (212, 214) change, as indicated in block (478), processing unit (308) may then adjust the firing motor (306) as shown in block (480).

D. Exemplary Algorithm for Determining End-of-Life of Robotic Surgical Instrument As mentioned above, surgical instruments (110) being used during a procedure may be used in accordance with the description herein, removed from robotic arm (342), and then replaced such that another instrument (110) is loaded back onto robotic arm (342). For instance, assistant(s) (20) may remove surgical instrument (110) having end effector (116, 210) from patient side cart (22) and replace surgical instrument (110) with another surgical instrument (110) from a tray (30) (shown in FIG. 1) in the operating room. The recently removed surgical instrument (110) may have a spent end effector (116, 210). In other words, the recently removed surgical instrument (110) may have an end effector (116, 210) that has been fired in accordance with the description herein in order to sever and staple grasped tissue. In such instances, surgical instrument (110) may be reloaded with another staple cartridge (154, 218), reattached to robotic arm (342), and then used for another cycle in order to sever and staple tissue in accordance with the teachings herein.

In some instances, a specific surgical instrument (110) may have components that wear-down after being used for multiple firing cycles. Additionally, a specific surgical instrument (110) may encounter unique operating conditions such that one specific surgical instrument (110) may wear-down faster compared to another specific surgical instrument (110). For instances, a specific surgical instrument (110) may require robotic motors (304, 306) to exceed their determined motor current limit during use of surgical instrument (110) for a specific use cycle. As another example, a specific surgical instrument (110) may experience an algorithmic bumping cycle (360) during a specific use cycle.

Therefore, it may be desirable to track noteworthy events affecting the use-life of a specific surgical instrument (110) in order to (A) determine desirable operating parameters for the next use of a specific surgical instrument (110), and (B) to determine the end-of-life of a specific surgical instrument (110) such that it is recommended that surgical instrument (110) not be used for another cycle in accordance with the description herein.

Additionally, as mentioned above, processing unit (308) may measure or receive operating data of robotic motors (304, 306) during exemplary use, transmit such data to a suitable storage device (310) (which may be associated with a specific instrument (110), robotic arm (342), or another suitable component of robotic surgical system (10)), and then recall such stored data for later use. Processing unit (308) and storage device (310) may store operating data of robotic motors (304, 306) accumulated during exemplary use of a specific instrument (110). As also mentioned above, processing unit (308) may be configured to determine when a noteworthy event occurred during operation of a specific instrument (110) and communicate such a noteworthy event to storage device (310) such that processing unit (308) may recall and utilize such noteworthy events when the specific instrument (110) is recoupled and reused with robotic arm (342) in accordance with the teachings herein.

Figure 24:
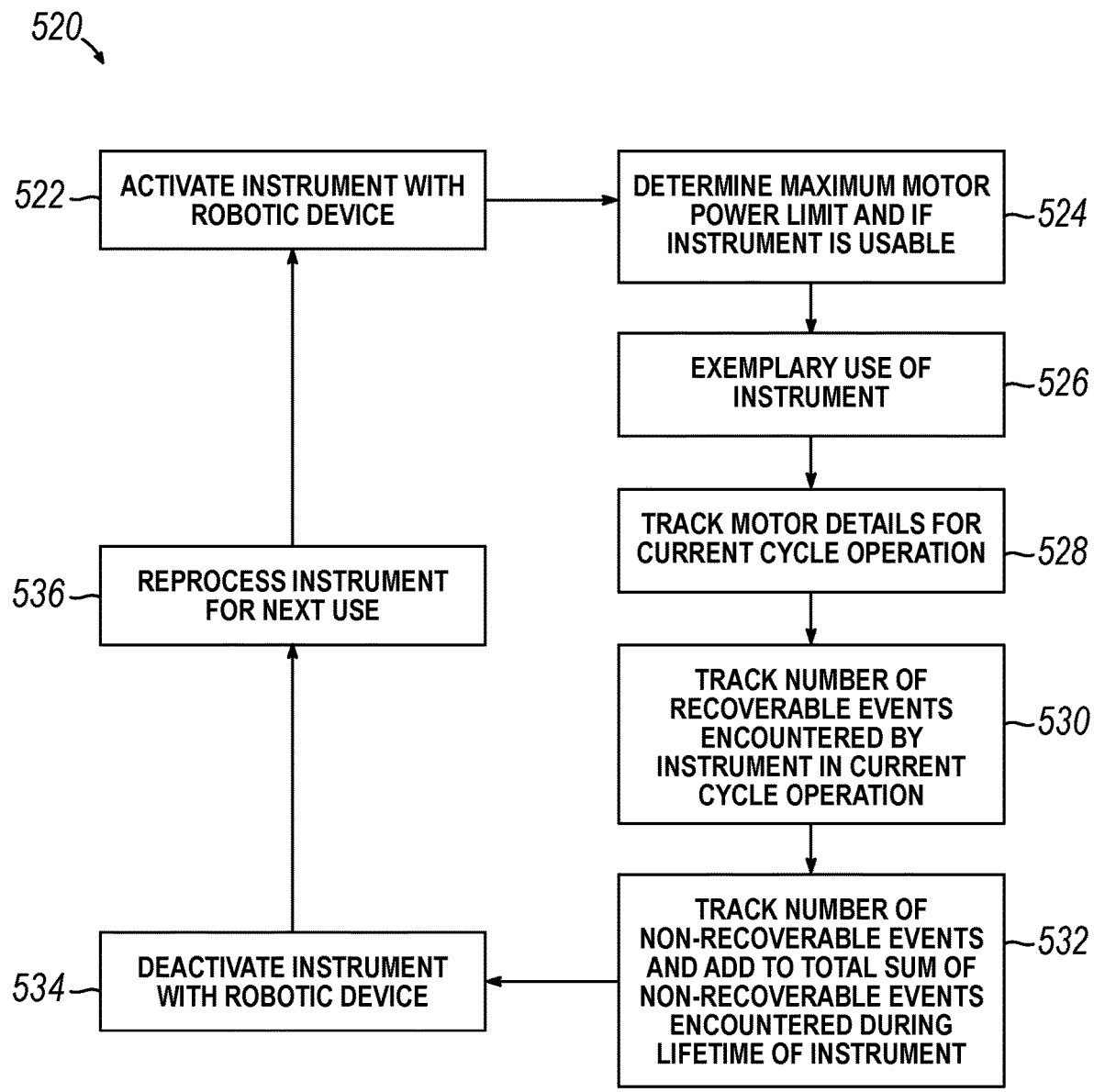
FIG. 24 depicts a block diagram of an exemplary end-of-life algorithm that may be used by the robotic arm and surgical instrument shown in FIG. 12.

Therefore, processing unit (308) may be configured to utilize the exemplary end-of-life algorithm (520) shown in FIG. 24. FIG. 25 shows an exemplary data table (540) that may be utilized by processing unit (308) in order to determine (A) operating parameters for motors (304, 306) during use a specific instrument (110) during a specific cycle, and (B) whether or not the specific instrument (110) should be used again in accordance with the description herein (i.e., the end-of-life of instrument (110)).

First, as shown in block (522), an operator may couple a specific instrument (110) with robotic arm (342) for exemplary use. After instrument (110) is coupled with robotic arm (342), as shown in block (524), processing unit (308) use data obtained from previous uses of the specific instrument (110) to determine the operating parameters of motor (such as max motor power limit) and/or if specific instrument (110) should not be used again. If it is determined that the specific instrument (110) should not be used again, processing unit (308) may notify a user that instrument (110) has reached its end-of-life and should not be used again and/or lock out further use of instrument (110).

Processing unit (308) may determine if the specific instrument (110) should not be used again using any suitable criteria as would be apparent to one skilled in the art in view of the teachings herein. For example, if the max motor power limit determined by processing unit (308) for a specific instrument (110) is below a predetermined threshold, then processing unit (308) may determine instrument (110) has reached its end-of-life. As another example, if an accumulative number of events occurs for a specific noteworthy category (such a sum of non-recoverable events), then processing unit (308) may determine instrument (110) has reached its end-of-life. It should be understood processing unit (308) may determine the reduction in max motor power limit by accumulating any data or noteworthy events that would be apparent to one skilled in the art in view of the teachings herein. Additionally, each category of noteworthy events may have their own weight in determining the operating parameters of motors (304, 306) during the next use, or if instrument (110) should even be used at all.

As an example, processing unit (308) may collect data in the form of a data table (540). Processing unit (308) may access data table (540) after previous uses of a specific instrument (110) to determine the motor power limits that should be established for the upcoming use cycle.

Referencing data table (540), when specific instrument (110) was coupled to robotic arm (342) for the second use cycle, data collected during the first use cycle was used to drop the maximum motor power limit from 100% to 93%. This reduction was based on (A) the previous use of instrument, and (B) the fact processing unit (308) detected four "non-recoverable" events during the first usage. When specific instrument (110) was coupled to robotic arm (342) for the third use cycle and the sixth use cycle, a reduction in maximum motor power limit occurred due to (A) the previous use of instrument, and (B) the fact processing unit (308) detected "recoverable" events during the first usage. In some instances, and shown between uses four and five, max motor power limits may drop due to accumulations within the "cycle operation counts" category, such as experiencing a moment where robotic motors (304, 306) excess an electrical current limit, a temperature limit, undergo an algorithmic bumping cycle (360), or experience a passive "wait period" to allow for the milking effect to reduce the requiring firing force.

The difference between "non-recoverable" events and "recoverable" events may be determined by the degree of severity such an event has on the impact the specific instrument (110). For instance, a recoverable even may include the severing knife (172) coming into contact with a clip or other item that is not the intended tissue, while a non-recoverable even may be more sever.

If the specific instrument (110) is determined suitable for another use cycle the operator may use instrument (110) in accordance with the description herein, as shown in block (526). During exemplary use, processing unit (308) may track motor details for the current cycle operation, as shown in block (528). Additionally, processing gun it (308) may track the number of recoverable events for the current cycle operation, as shown in block (530). Also, processing unit may track the number of non-recoverable events during a current cycle and add those to the sum of non-recoverable events encountered previously during the lifetime of the instrument (110), as indicted in block (532).

After use of instrument (110), instrument (110) may be detached from robotic arm (342) and reprocessed for next use as indicated in blocks (534, 536). Processing unit (308) may then add the data information related to the current cycle used to data table (540) in order to use such data in determining potential end-of-life of instrument (110) during next use, or in determining the new operating partakers of robotic arm (342) for the next use of instrument (110).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) an end effector, the end effector including: (i) a body, (ii) a blade, (iii) a plurality of staples, and (iv) a firing member, the firing member being operable to one or both of drive the blade through tissue or drive the plurality of staples into tissue; (b) a motor operable to drive the firing member; and (c) a processing unit configured to: (i) activate the motor to distally advance the firing member within the body of the end effector, (ii) detect an initiation condition, and (iii) in response to detecting the initiation condition, activate an algorithmic bumping mode, the algorithmic bumping mode comprising: (A) activating the motor to advance the firing member distally with a first plurality starting and stopping motions at a first rate and a first power level, and (B) activating the motor to retract the firing member proximally with a second plurality of starting and stopping motions at a second rate and a second power level, wherein the first rate is different than the second rate, wherein the first power level is different than the second power level.

Example 2

The apparatus of Example 1, wherein the initiation condition is based, at least partially, on how many cycles the firing member has been previously used.

Example 3

The apparatus of any of Examples 1 through 2, wherein the first rate and the first power level are based, at least partially, on how many cycles the firing member has been previously used.

Example 4

The apparatus of Example 3, wherein the second rate and the second power level are each based, at least partially, on how many cycles the firing member has been previously used.

Example 5

The apparatus of any of Examples 1 through 4, wherein the processing unit is further configured such that activating the motor to advance the firing member distally with the first plurality of starting and stopping motions will occur prior to activating the motor to retract the firing member proximally with the second plurality of starting and stopping motions.

Example 6

The apparatus of any of Examples 1 through 5, wherein the initiation condition is a predetermined power level used by the motor to distally advance the firing member.

Example 7

The apparatus of any of Examples 1 through 6, wherein the second power lever is greater than the first power level.

Example 8

The apparatus of any of Examples 1 through 7, wherein the first rate is greater than the second rate.

Example 9

The apparatus of any of Examples 1 through 8, wherein the processing unit is configured such that the first plurality starting and stopping motions will occur at a first frequency, wherein the processing unit is further configured such that the second plurality of starting and stopping motions will occur at a second frequency.

Example 10

The apparatus of Example 9, wherein the first frequency is greater than the second frequency.

Example 11

The apparatus of any of Examples 1 through 10, wherein the end effector further comprises a first jaw and a second jaw configured to pivot relative to each other.

Example 12

The apparatus of Example 11, wherein the firing member is configured to drive the first jaw and the second jaw to pivot toward each other as the firing member advances distally.

Example 13

The apparatus of any of Examples 1 through 12, further comprising a staple cartridge, the staple cartridge containing the plurality of staples.

Example 14

The apparatus of Example 13, wherein the staple cartridge further contains the blade.

Example 15

The apparatus of any of Examples 1 through 14, further comprising a robotic arm, the end effector being positioned at a distal end of the robotic arm.

Example 16

A method of firing an end effector with a motor, wherein the motor is configured to drive a firing member within the end effector to staple and sever tissue grasped by the end effector, the method comprising: (a) distally advancing the firing member within the end effector; (b) detecting a firing resistance above a predetermined threshold; and (c) in response to detecting the firing resistance above the predetermined threshold, activating a bumping mode, the bumping mode comprising: (i) advancing the firing member distally with a first plurality starting and stopping motions, and (ii) retracting the firing member proximally with a second plurality of starting and stopping motions.

Example 17

The method of Example 16, wherein advancing the firing member distally with a first plurality starting and stopping motions comprises activating and deactivating the motor, respectively, a plurality of times.

Example 18

The method of any of Examples 16 through 17, wherein the first plurality of starting and stopping motions occurs at a first power level for the motor, wherein the second plurality of starting and stopping motions occurs at a second power level for the motor.

Example 19

The method of any of Examples 16 through 18, further comprising fully advancing the firing member after completion of the bumping mode.

Example 20

A method of firing a robotically controlled end effector with a motor, wherein the motor is configured to drive a firing member within the end effector to advance a blade through the end effector or fire a plurality of staples out of a replaceable staple cartridge, the method comprising: (a) determining a maximum power level for motor to advance the firing member; (b) distally advancing the firing member within the end effector; (c) activating the motor at the maximum power level; and (d) in response to activating the motor at the maximum power level, activating an algorithmic bumping mode, the algorithmic bumping mode comprising: (i) advancing the firing member distally with a plurality starting and stopping motions, and (ii) retracting the firing member proximally with a plurality of starting and stopping motions.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, published as U.S. Pub. No. 2023/0051271 on Feb. 16, 2023; U.S. patent application Ser. No. 17/402,679, entitled "Powered Surgical Stapler Having Independently Operable Closure and Firing Systems," filed on Aug. 16, 2021, published as U.S. Pub. No. 2023/0051756 on Feb. 16, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,703, entitled "Proximally Located Firing Lockout Mechanism for Surgical Stapler," filed on Aug. 16, 2021, published as U.S. Pub. No. 2023/0051105 on Feb. 16, 2023; U.S. patent application Ser. No. 17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No. 17/402,732, entitled "Sled Restraining Member for Surgical Stapler," filed on Aug. 16, 2021, published as U.S. Pub. No. 2023/0045893 on Feb. 16, 2023; U.S. patent application Ser. No. 17/402,738, entitled "Firing Member Tracking Feature for Surgical Stapler," filed on Aug. 16, 2021, published as U.S. Pub. No. 2023/0049736 on Feb. 16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an end effector, the end effector including:
      (i) a body,
      (ii) a blade,
      (iii) a plurality of staples, and
      (iv) a firing member, the firing member being operable to one or both of drive the blade through tissue or drive the plurality of staples into tissue;
   (b) a motor operable to drive the firing member; and
   (c) a processor configured to:
      (i) activate the motor to distally advance the firing member within the body of the end effector,
      (ii) detect an initiation condition, and
      (iii) in response to detecting the initiation condition, activate an algorithmic bumping mode, the algorithmic bumping mode comprising:
         (A) activating the motor to advance the firing member distally with a first plurality starting and stopping motions at a first frequency and a first power level, and
         (B) activating the motor to retract the firing member proximally with a second plurality of starting and stopping motions at a second frequency and a second power level, wherein the first power level is different than the second power level.

2. The apparatus of claim 1, wherein the initiation condition is based, at least partially, on how many cycles the firing member has been previously used.

3. The apparatus of claim 1, wherein the first power level is based, at least partially, on how many cycles the firing member has been previously used.

4. The apparatus of claim 3, wherein the second power level is each based, at least partially, on how many cycles the firing member has been previously used.

5. The apparatus of claim 1, wherein the processor is further configured such that activating the motor to advance the firing member distally with the first plurality of starting and stopping motions will occur prior to activating the motor to retract the firing member proximally with the second plurality of starting and stopping motions.

6. The apparatus of claim 1, wherein the initiation condition is a predetermined power level used by the motor to distally advance the firing member.

7. The apparatus of claim 1, wherein the second power lever is greater than the first power level.

8. The apparatus of claim 1, wherein the first frequency is greater than the second frequency.

9. The apparatus of claim 1, wherein the end effector further comprises a first jaw and a second jaw configured to pivot relative to each other.

10. The apparatus of claim 9, wherein the firing member is configured to drive the first jaw and the second jaw to pivot toward each other as the firing member advances distally.

11. The apparatus of claim 1, further comprising a staple cartridge, the staple cartridge containing the plurality of staples.

12. The apparatus of claim 11, wherein the staple cartridge further contains the blade.

13. The apparatus of claim 1, further comprising a robotic arm, the end effector being positioned at a distal end of the robotic arm.

14. The apparatus of claim 1, wherein the first frequency is limited between the first power level and an inactive power level, wherein the second frequency is limited between the second power level and the inactive power level.

15. A method of firing an end effector with a motor, wherein the motor is configured to drive a firing member within the end effector to staple and sever tissue grasped by the end effector, the method comprising:
- distally advancing the firing member within the end effector;
- detecting a firing resistance above a predetermined threshold;
- in response to detecting the firing resistance above the predetermined threshold, activating a bumping mode, the bumping mode comprising:
  - advancing the firing member distally with a first plurality starting and stopping motions, and
  - retracting the firing member proximally with a second plurality of starting and stopping motions; and
- fully advancing the firing member after completion of the bumping mode.

16. The method of claim 15, wherein advancing the firing member distally with a first plurality starting and stopping motions comprises activating and deactivating the motor, respectively, a plurality of times.

17. The method of claim 15, wherein the first plurality of starting and stopping motions occurs at a first power level for the motor, wherein the second plurality of starting and stopping motions occurs at a second power level for the motor.

18. The apparatus of claim 15, wherein the second plurality of starting and stopping motions occurs sequentially after the first plurality of starting and stopping motions occurs.

19. A method of firing a robotically controlled end effector with a motor, wherein the motor is configured to drive a firing member within the end effector to advance a blade through the end effector or fire a plurality of staples out of a replaceable staple cartridge, the method comprising:
- determining a maximum power level for motor to advance the firing member;
- distally advancing the firing member within the end effector;
- activating the motor at the maximum power level; and
- in response to activating the motor at the maximum power level, activating an algorithmic bumping mode, the algorithmic bumping mode comprising:
  - advancing the firing member distally with a plurality starting and stopping motions at a first frequency, and
  - retracting the firing member proximally with a plurality of starting and stopping motions at a second frequency that is different than the first frequency.

* * * * *